(12) United States Patent
De La Sema et al.

(10) Patent No.: US 7,654,983 B2
(45) Date of Patent: Feb. 2, 2010

(54) PNEUMATIC POWERED AUTOINJECTOR

(75) Inventors: Pedro E. De La Sema, San Jose, CA (US); Scott J. Gilbert, Menlo Park, CA (US)

(73) Assignee: Johnson and Johnson Vision Care, Inc., Jacksonville, FL (US)

( * ) Notice: Subject to any disclaimer, the term of this patent is extended or adjusted under 35 U.S.C. 154(b) by 511 days.

(21) Appl. No.: 10/290,914

(22) Filed: Nov. 8, 2002

(65) Prior Publication Data

US 2003/0233070 A1    Dec. 18, 2003

Related U.S. Application Data

(60) Provisional application No. 60/337,753, filed on Nov. 9, 2001.

(51) Int. Cl.
    *A61M 37/00*  (2006.01)
(52) U.S. Cl. .................... 604/141; 604/506
(58) Field of Classification Search ............ 604/141, 604/143, 187, 218, 239, 272, 68–70, 73, 604/140, 146–149, 506, 500
    See application file for complete search history.

(56) References Cited

U.S. PATENT DOCUMENTS

| | | | |
|---|---|---|---|
| 2,752,918 A | | 7/1956 | Uytenbogaart |
| 3,403,680 A | | 10/1968 | Watson et al. |
| 3,688,765 A | * | 9/1972 | Gasaway .................. 604/143 |
| 3,797,489 A | | 3/1974 | Sarnoff |
| 4,031,889 A | * | 6/1977 | Pike ........................ 604/144 |
| 4,790,824 A | * | 12/1988 | Morrow et al. ........... 604/143 |
| 5,137,516 A | | 8/1992 | Rand et al. |
| 5,176,645 A | | 1/1993 | Guerrero |
| 5,300,030 A | | 4/1994 | Crossman et al. |
| 5,328,481 A | * | 7/1994 | Wang ...................... 604/506 |
| 5,352,196 A | | 10/1994 | Haber et al. |
| 5,425,715 A | | 6/1995 | Dalling et al. |
| 5,520,639 A | | 5/1996 | Peterson et al. |
| 5,527,287 A | | 6/1996 | Miskinyar |

(Continued)

FOREIGN PATENT DOCUMENTS

EP    0 295 917 A    12/1988

(Continued)

*Primary Examiner*—Nicholas D Lucchesi
*Assistant Examiner*—Theodore J Stigell
(74) *Attorney, Agent, or Firm*—Todd Volyn

(57) ABSTRACT

The present invention provides a pneumatic injector that includes a pressurized gas source, an actuator, a driver, and a dispenser. The dispenser of the injector includes a reservoir for containing a desired amount of a chosen medicament and a needle, such as a hypodermic needle, suitable for subcutaneous, intramuscular, or intra-articular delivery of the chosen medicament. The actuator actuates the transmission of pressurized gas from the pressurized gas source to the driver, and as pressurized gas is delivered to the driver, the driver exerts at least an injection force. The injection force is of sufficient magnitude to expel a chosen medicament through the needle of the dispenser within a desired amount of time. Advantageously, the design of the injector of the present invention is extremely flexible, allowing the injector to be designed to deliver a wide range of medicaments in virtually any human or veterinary context calling for the injection of the subcutaneous, intramuscular, or intra-articular injection of medicament.

21 Claims, 19 Drawing Sheets

U.S. PATENT DOCUMENTS

| | | | |
|---|---|---|---|
| 5,741,275 A * | 4/1998 | Wyssmann | 604/143 |
| 5,779,677 A | 7/1998 | Frezza | |
| 5,792,099 A * | 8/1998 | DeCamp et al. | 604/506 |
| 5,845,811 A | 12/1998 | Shervington et al. | |
| 6,047,865 A | 4/2000 | Shervington et al. | |
| 6,270,479 B1 | 8/2001 | Bergens et al. | |
| 6,447,482 B1 | 9/2002 | Rønborg et al. | |
| 6,569,123 B2 | 5/2003 | Alchas et al. | |
| 2001/0005781 A1 | 6/2001 | Bergens | |

FOREIGN PATENT DOCUMENTS

| | | |
|---|---|---|
| EP | 0 897 728 | 2/1999 |
| EP | 1443992 B1 | 3/2007 |
| HU | 179577 B | 11/1982 |
| HU | 186718 B | 9/1985 |
| HU | 195428 B | 5/1988 |
| HU | 189198 B | 6/1990 |
| HU | 211712 B | 12/1995 |
| HU | 214350 B | 3/1998 |
| HU | 218191 B | 6/2000 |
| JP | 64-017654 U1 | 7/1987 |
| JP | 3-222962 | 10/1999 |
| JP | 2001-511404 A | 8/2001 |
| WO | WO94/13342 | 6/1994 |
| WO | WO95/31235 | 11/1995 |
| WO | WO99/06100 | 2/1999 |
| WO | WO 99/06100 A2 | 2/1999 |
| WO | WO 00/71185 A2 | 11/2000 |
| WO | WO 01/64269 A | 9/2001 |

\* cited by examiner

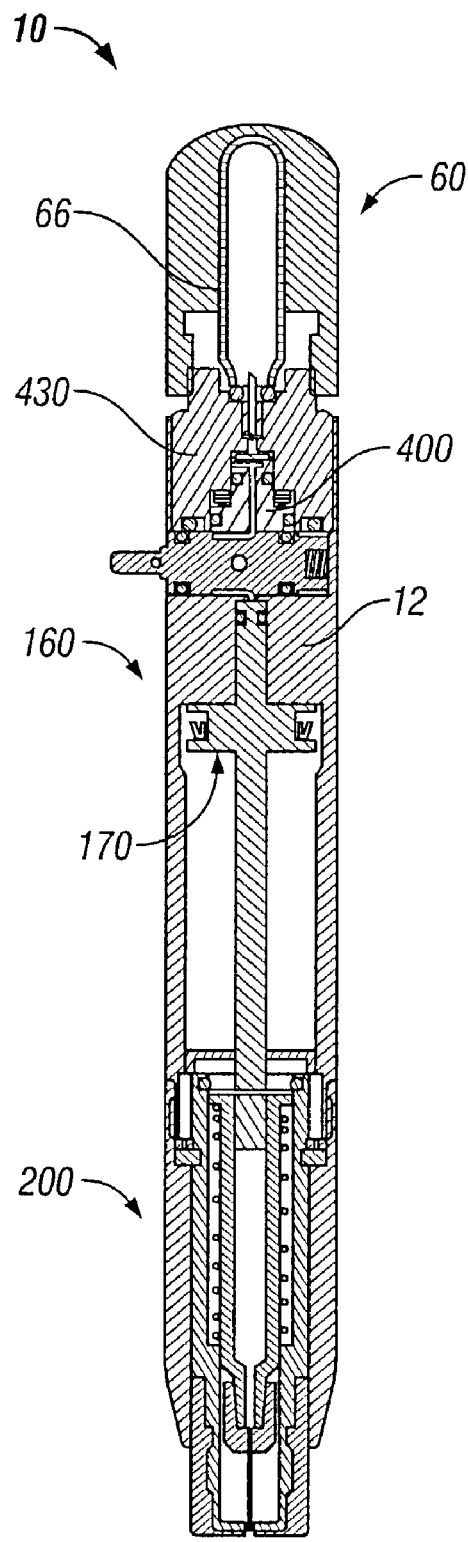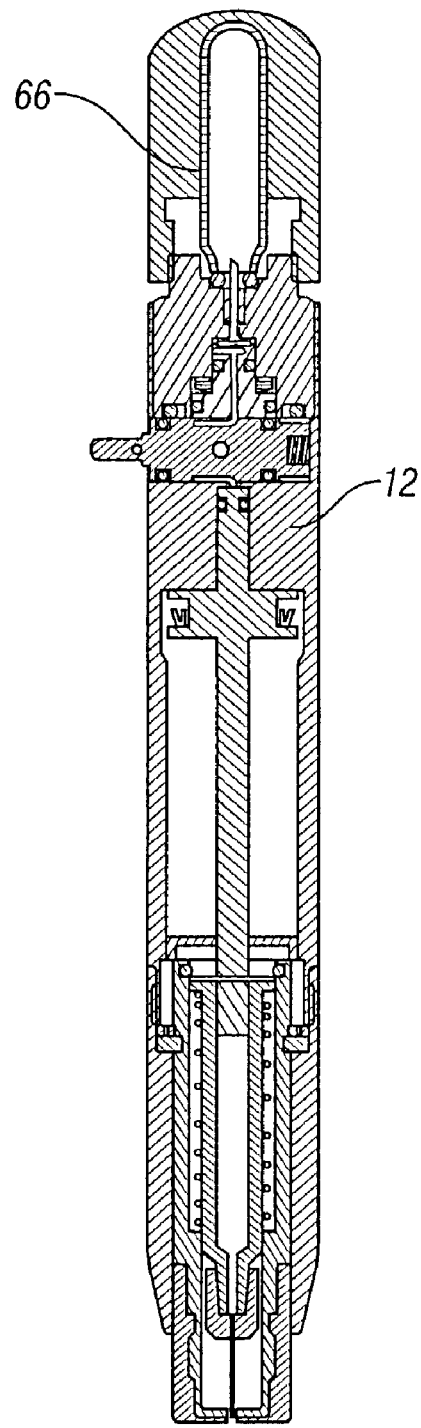
FIG. 10A
FIG. 10B

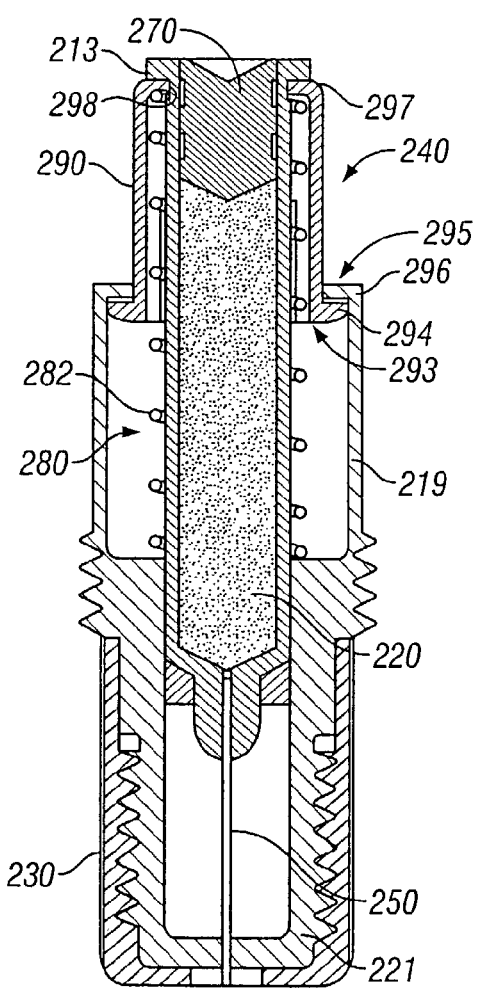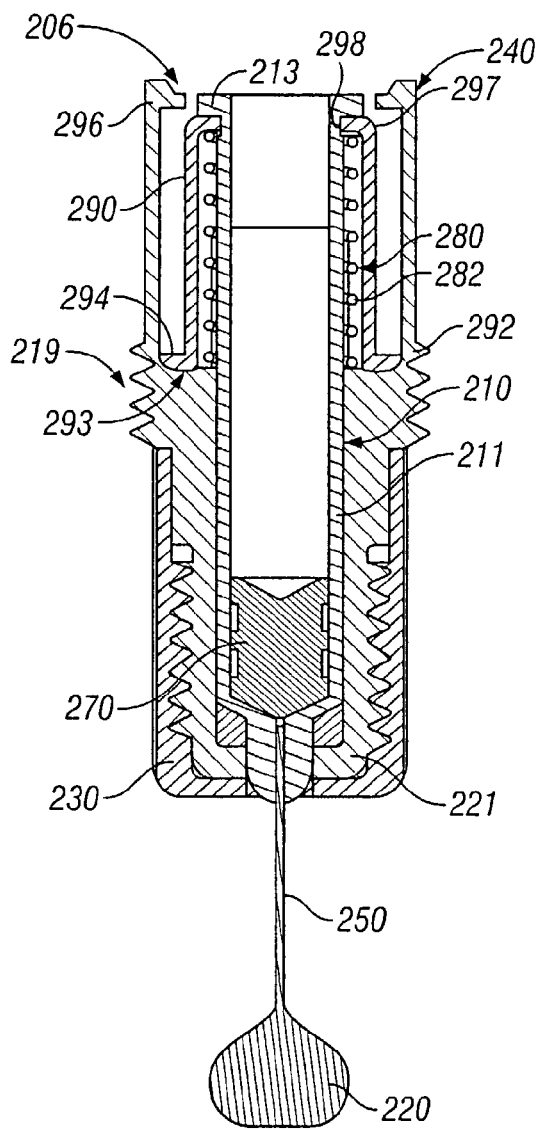
FIG. 18
FIG. 19

PNEUMATIC POWERED AUTOINJECTOR

RELATED CASES

This is a non-provisional application claiming priority under 35 U.S.C. § 119 from U.S. provisional application No. 60/337,753, filed on Nov. 9, 2001.

BACKGROUND

1. Field of the Invention

The present invention relates to devices for injecting medicaments into human or animal subjects. In particular, the present invention relates to an injector capable of delivering medicaments to animal and human subjects and to a method for delivering medicaments to animal or human subjects.

2. State of the Art

Automatic injectors (hereinafter referred to as "autoinjectors") are well known in the medical and veterinary industries and enable the automatic injection of a desired dose of medicament to animal or human subjects. Autoinjectors are generally designed according to one of two delivery mechanisms: those that deliver medicament using a needle (hereinafter "needled" autoinjectors); and those that do not (hereinafter "needle-less" autoinjectors). No matter what their design, autoinjectors are thought to exhibit several advantages relative to simple hypodermic syringes. For instance, because autoinjectors may be designed to automatically and reliably deliver a desired dose of medicament on demand, they facilitate quick, convenient, and accurate delivery of medicaments. In particular, autoinjectors are well suited for use by human subjects who must self-administer therapeutic substances. Moreover, where autoinjectors incorporate a needled injection mechanism, they may be designed so that the needle is hidden from view before, during, and after a delivery cycle, thereby reducing or eliminating any anxiety associated with the act of penetrating a visible needle into the subject's tissue. Various different injection devices are disclosed in U.S. Pat. Nos. 3,797,489, 5,176,645, 5,527,287, 5,300,030, and 6,270,479, U.S. patent application 20010005781, and International Publications WO 94/13342 and WO 95/31235.

Despite the benefits they provide, however, state of the art autoinjectors are not generally designed for delivery of viscous medicaments. Because the medicament delivered by needle-less autoinjectors is typically accelerated to a very high velocity (e.g., 800 feet per second (fps) to 1,200 fps) to effect injection, needle-less autoinjectors are not well suited for the delivery of viscous medicaments or medicaments incorporating particles larger than a few microns in any dimension. Moreover, autoinjectors including needled injection mechanisms are generally designed to deliver aqueous solutions having very low viscosities, such as insulin or epinephrine solutions, and, therefore, do not typically address the performance hurdles presented when seeking to deliver viscous medicament via a needled injection mechanism.

Generating an injection force of sufficient magnitude to drive a viscous medicament through a needle of suitable gauge within a suitable amount of time is one performance hurdle that must be overcome in order to deliver a viscous medicament via a needled injection device. To ensure the safety and comfort of the subject, the gauge of the needles used in needled injection devices typically ranges from about 21 gauge to about 31 gauge. Yet, a number of existing and emerging medicaments designed for delivery via subcutaneous, intramuscular, or intra-articular injection exhibit viscosities that range up to and above 10 Poise, 100 Poise, 1,000 Poise, and even 10,000 Poise. As is easily appreciated by reference to the Hagen-Poiseuille Law, $F=8Q\mu L(R^2/r^4)$, wherein "F" represents the injection force required, "Q" represents the flow rate of the material injected, "$\mu$" represents the viscosity of the material injected, "L" represents the length of the needle used, "R" represents the internal diameter of the reservoir containing the material to be injected, and "r" represents the internal diameter of the needle used, injection of such medicaments through a needle of suitable gauge may require an injection force that approaches or exceeds 100 pounds. For example, the Hagen-Poiseuille Law indicates that in order to deliver 0.5 cc of a medicament having a viscosity of 200 Poise within 10 seconds via a syringe having an internal diameter of 4.5 mm and a 0.5 inch needle having an internal diameter of 0.012 inches (a 24 gauge needle), an injection force of approximately 100 pounds would be required. However, the injection mechanisms provided in currently available needled autoinjectors are generally not designed to generate such high injection forces.

Subject discomfort is a second hurdle facing the design of a needled autoinjector capable of delivering viscous medicaments. For instance, the sudden application of a force suitable for delivering a viscous medicament via a needle of suitable gauge may startle the subject, particularly if the application of such force causes the transmission of noticeable recoil or impact forces. Thus, an injector capable of delivering viscous medicaments would ideally incorporate a driver that operates without producing sudden, potentially distressing noises or transmitting significant recoil or impact forces to the subject. In addition, driving a needle into the subject with the same force required to drive a viscous medicament through a needle of desired gauge may cause the subject unnecessary physical discomfort. For instance, where the gauge of the needle ranges from about 21 to 31 gauge, an insertion force ranging from about 1 to 7 pounds is believed to be most comfortable. Some studies even suggest that human subjects experience the least amount of pain when the needle is inserted with the least amount of force necessary. Therefore, in order to minimize or reduce the discomfort of the intended subject, an injector capable of injecting viscous medicaments should not only operate unobtrusively, but, where desired, the injector should be capable of inserting a needle with an insertion force tailored to minimize subject discomfort. Ideally, such an injector would generate both an insertion force and an injection force sufficient to deliver a viscous medicament through a needle of desired gauge within a suitable amount of time using a single driving mechanism.

SUMMARY OF THE INVENTION

The present invention provides a needled injector that may be used to deliver medicaments exhibiting a wide range of viscosities to human or animal subjects. In the context of the present invention, the term "viscosity" refers to the resistance of a material to sheer forces as measured at a 1.0 sec-1 shear rate and 25° C. using a Haake Rheometer, the term "viscous" is used to define medicaments having a viscosity of about 1 Poise or greater as measured at a 1.0 sec-1 shear rate and 25° C. using a Haake Rheometer, and the term "medicament" is used to define any beneficial agent that may be administered by injection to either a human or animal subject. For example, medicaments that may be delivered using the injector of the present invention include liquids, suspensions, gels, solutions, slurries, and pastes containing any physiologically or pharmacologically active substance, or any other substance that may be of value in treating or caring for human or animal subjects.

In each of its embodiments, the injector of the present invention may be designed to generate an injection force of sufficient magnitude to deliver a viscous medicament through a needle of suitable gauge within a chosen amount of time. Where desired, the injector of the present invention may be designed to drive the needle of the injector into the tissue of the subject with an insertion force that is tailored to minimize subject discomfort. Advantageously, the operation of the injector of the present invention is simple, quiet, and does not result in the transmission of noticeable recoil or impact forces. In addition, the design of the injector is extremely flexible, allowing the injector for use in virtually any context calling for the subcutaneous, intramuscular, or intra-articular injection of a medicament. Therefore, not only can an injector of the present invention be designed to deliver a wide range of medicaments, even viscous medicaments, but the injector of the present invention operates unobtrusively, thereby serving to minimize any anxiety experienced by the subject.

The present invention also includes a method of injecting medicament. In each of its embodiments, the method of the present invention includes providing a desired medicament, providing a needle of a desired gauge, inserting the needle into the tissue of the subject, and generating an injection force sufficient to drive the medicament through the needle and into the tissue of the subject. Though the medicament provided in the method of the present invention may exhibit any viscosity, the method of the present invention preferably includes providing a viscous medicament. The gauge and length of the needle provided and used in the method of the present invention will depend upon, for example, the medicament delivered, the proposed subject, and whether the injection is subcutaneous, intramuscular, or intra-articular. Nevertheless, the gauge and length of the needle are preferably chosen to minimize subject discomfort. Further, the injection force generated in the method of the present invention must be sufficient to deliver a desired dose of the provided medicament within a suitable amount of time. Preferably, the injection force generated in the method of the present invention is sufficient delivering a desired dose of a chose medicament within, 10 seconds, and even more preferably within 5 seconds. The exact magnitude of the injection force generated in the method of the present invention, however, depends on various factors, such as the medicament chosen, the length an gauge of the needle chosen and the desired delivery time.

The method of the present invention may further include providing an insertion force, which is less than the injection force. The insertion force may be tailored to minimize subject discomfort as the needle is inserted into the tissue of the subject. For example, where the intended subject is human and the gauge of the needle provided ranges from between 21 gauge and 31 gauge, an insertion force of between about 1 pound and 7 pounds is preferred, with an injection force of between about 1 and 4 pounds being even more preferable. However, where the method of the present invention involves providing an insertion force, the magnitude of the insertion force will vary according to several factors, such as the anticipated subject, the gauge of the needle used to deliver the medicament, and whether the injection is to be subcutaneous, intramuscular, or intra-articular.

BRIEF DESCRIPTION OF THE DRAWINGS

FIG. 10a illustrates an injector according to the present invention that incorporates a pressure regulator.

FIG. 10b illustrates an injector according to the present invention that incorporates a pressure regulator and a restrictor.

FIG. 16 through FIG. 22 illustrate a collapsible syringe cartridge that may be used as a dispenser for an injector of the present invention.

DETAILED DESCRIPTION OF PREFERRED EMBODIMENTS

Figure 1:
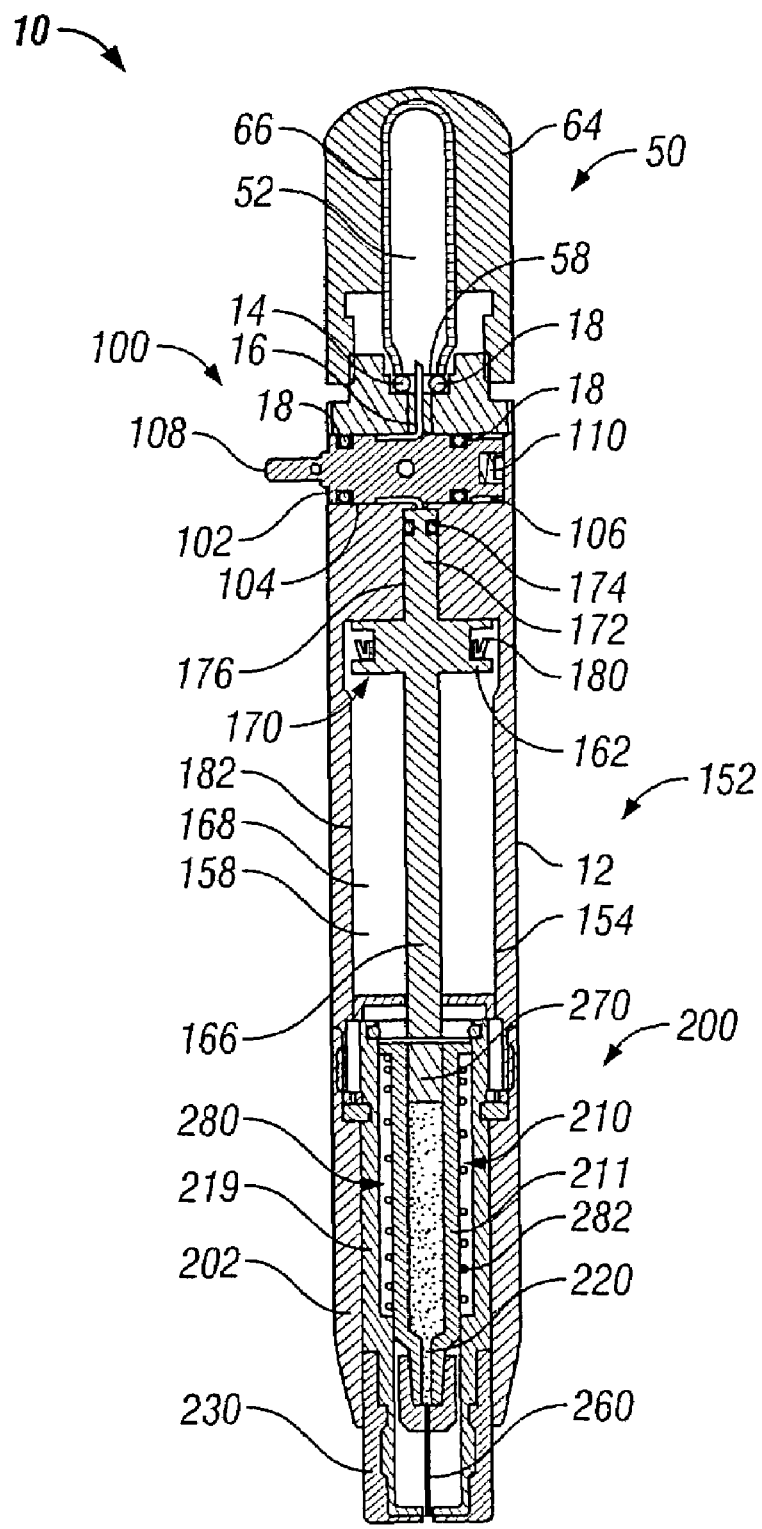
FIG. 1 illustrates an injector according to the present invention including a multistage driver and an actuator including a valve mechanism.

The injector 10 of the present invention includes a pressurized gas source 50, an actuator 100, a driver 150, and a dispenser 200. The dispenser 200 of the injector 10 includes a reservoir 210 for containing a desired amount of a chosen medicament 220 and a needle 250, such as a hypodermic needle, suitable for subcutaneous, intramuscular, or intra-articular delivery of the chosen medicament 220. The actuator 100 actuates the transmission of pressurized gas from the pressurized gas source 50 to the driver 150, and as pressurized gas is delivered to the driver 150, the driver 150 exerts at least an injection force. The injection force is of sufficient magnitude to expel the medicament 220 through the needle 250 of the dispenser 200 within a desired amount of time. Advantageously, the design of the injector 10 of the present invention is extremely flexible, allowing the injector 10 to be designed to deliver a wide range of medicaments in virtually any human or veterinary context calling for the injection of the subcutaneous, intramuscular, or intra-articular injection of medicament. An exemplary injector 10 according to the present invention is illustrated in FIG. 1.

Figure 3:
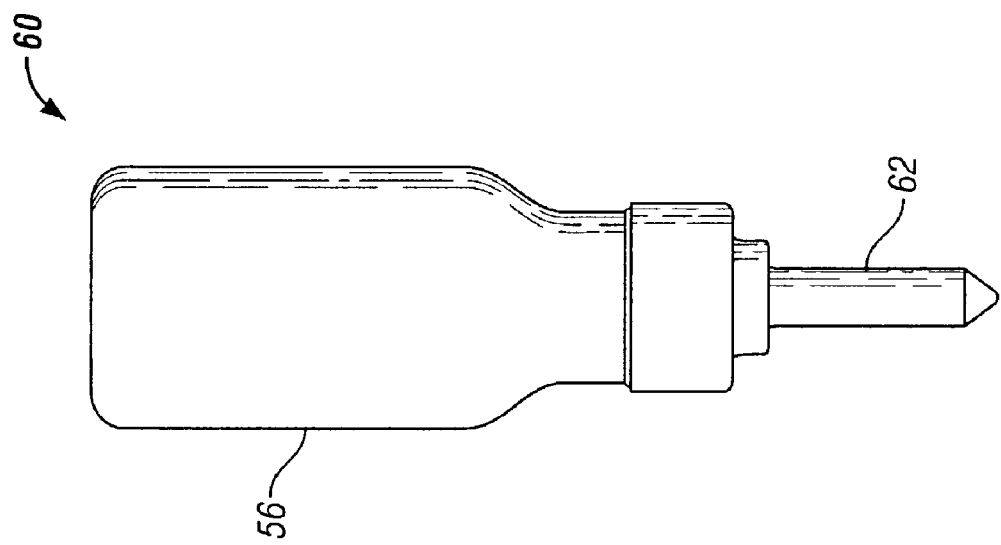
FIG. 3 illustrates a break-away microcylinder.
Figure 2:
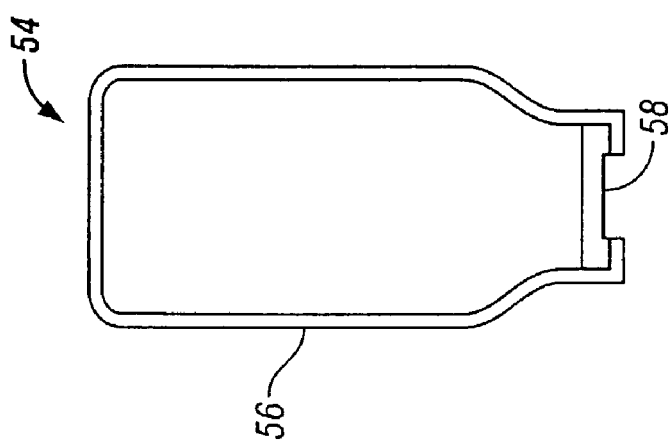
FIG. 2 illustrates a sealed microcylinder.

Though any suitable source of pressurized gas may be used as the pressurized gas source 50 of the injector 10 of the present invention, it is presently preferred that the pressurized gas source 50 includes a microcylinder 52 of compressed gas. Microcylinders are economical, compact, and capable of storing varying amounts of gas at high pressures. For example, commercially available microcylinders can be reliably and inexpensively filled with about 1 gram to about 30 grams of a suitable gas, such as carbon dioxide, helium, hydrogen, oxygen, nitrogen, or air, at pressures ranging between about 200 pounds per square inch ("psi") to about 3,000 psi and above. Moreover, microcylinders having such capabilities can be extremely compact, having a length of one inch or less and a diameter of one-half inch or less. Therefore, a microcylinder 52 of pressurized gas provides a powerful, economical source of pressurized gas that allows the fabrication of an injector that is highly portable 10 and easy to use.

Where a microcylinder is utilized in conjunction with the injector of the present invention, two general microcylinder designs are presently preferred. The first general design 54 (hereinafter referred to as a "sealed microcylinder") is illustrated in FIG. 2, and is exemplified by microcylinders having a cylinder body 56 and a seal 58. Such microcylinders are available from Leland Limited, Inc., of South Plainfield, N.J. In order to release compressed gas maintained within a sealed microcylinder, the seal 58 must be compromised (e.g., broken, pierced, or otherwise penetrated). The second general microcylinder design 60 (hereinafter referred to as "breakaway microcylinders") is shown in FIG. 3 and is exemplified by microcylinders that include an elongated neck 62 extending away from a cylinder body 56, the elongated neck 62 being designed to break away upon application of a predetermined force. Such microcylinders are described in U.S. Pat. No. 6,047,865 and U.S. Pat. No. 5,845,811 and are manufactured by BOC Limited of London, U.K. As is easily appreciated, compressed gas stored within a break-away microcylinder is released when the elongated neck 62 of the microcylinder is broken. Though each of the embodiments illustrated and discussed herein utilize either a sealed microcylinder or a breakaway microcylinder, the injector 10 of the present invention may be designed to utilize a microcylinder 52 of any suitable design.

Where a microcylinder 52 is used as the pressurized gas source 50 of the injector 10 of the present invention, the microcylinder 52 is preferably disposed within a cap 64. A cap 64 effectively increases the dimensions of the microcylinder 52 and thereby eases manipulation of the microcylinder 52 when the microcylinder 52 is not mounted to the body 12 of the injector 10. Where provided, a cap 64 is configured to receive a microcylinder 52 of desired configuration and may be designed to maintain the microcylinder 52 within the cap 64 via any suitable means. For instance, the caps 64 illustrated in FIG. 1, FIG. 4 through FIG. 10, and FIG. 25 and FIG. 26 are sized and shaped such that the microcylinders 52 disposed therein are maintained within the caps 64 by a friction fit created by the interface of the microcylinders 52 with the inner walls 66 of the caps 64. Though the caps 64 illustrated in FIG. 1, FIG. 4 through FIG. 10, and FIG. 25 and FIG. 26 are designed to receive and maintain sealed microcylinders or breakaway microcylinders, a cap 64 used in an injector 10 according to the present invention may be designed to receive and maintain a microcylinder 52 of any suitable design.

A cap 64 may also facilitate mounting of the microcylinder 52 to the body 12 of the injector 10 of the present invention. For example, the cap 64 may be configured to allow mounting of the cap 64 to the body 12 of the injector 10 using any bonding or adhesive process providing secure attachment of the cap 64 to the body 12 of the injector 10. Alternatively, the cap 64 may include a first portion of a fastening mechanism that is complimentary to a second portion of a fastening mechanism provided on the body 12 of the injector 10. For instance, the cap 64 may be provided with a first threaded area that is compatible with a second threaded area formed on the body 12 of the injector 10. Alternatively, the cap 64 may include a first portion of a snap-fit connector complimentary to a second portion of a snap fit connector provided on the body 12 of the injector 10. Further examples of fastening mechanisms that may be incorporated in a cap 64 and the body 12 of the injector 10 to facilitate mounting of the microcylinder 52 to the injector 10 are toggle assemblies and male/female connectors. However, it is to be understood that the cap 64 may incorporate any fastening mechanism capable of securely fastening the cap 64 to the body 12 of the injector 10.

Figure 5:
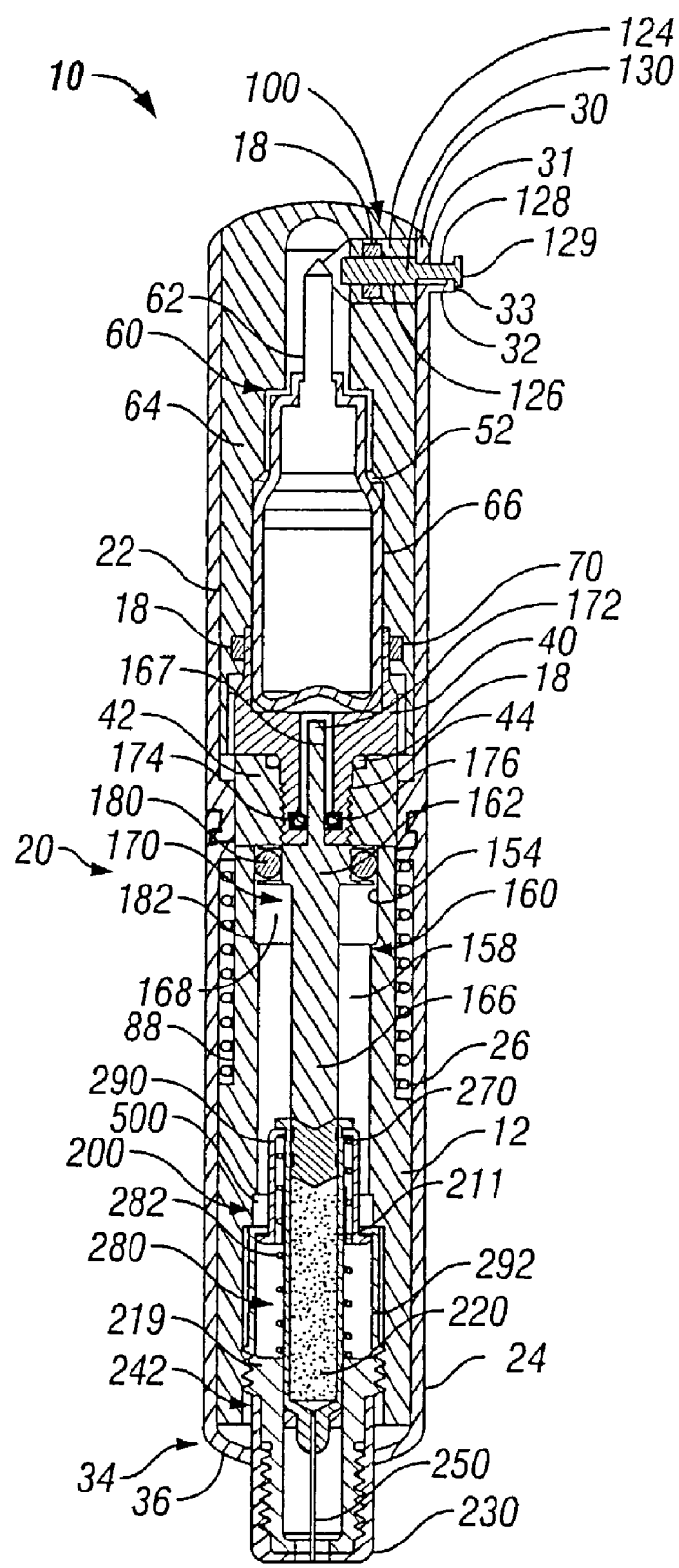
FIG. 5 illustrates an injector according to the present invention including a multistage driver and an actuator including a plunger mechanism.
Figure 6:
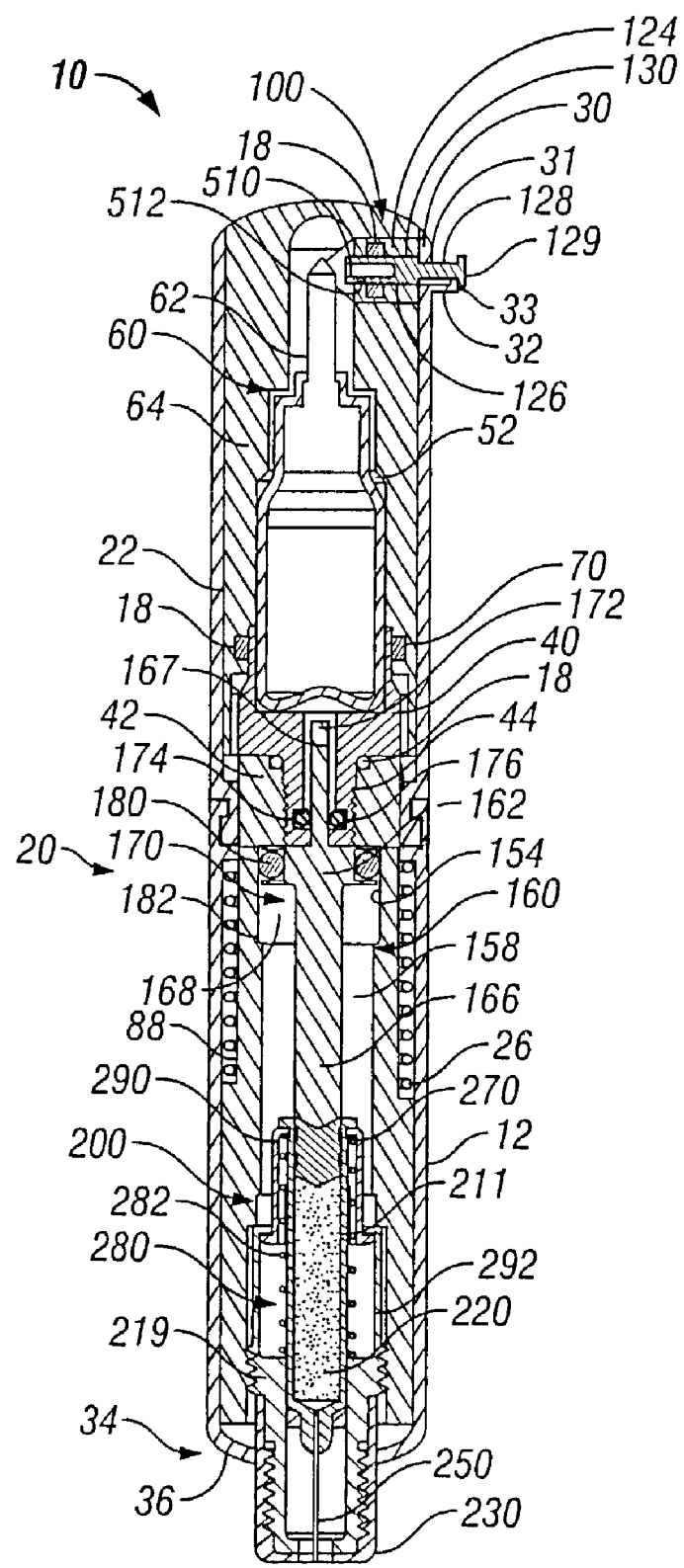
FIG. 6 illustrates an injector according to the present invention including a multistage driver and an actuator including a plunger mechanism.

In order to minimize the unwanted escape of pressurized gas from the injector 10 of the present invention, one or more sealing members 18 may be provided where the cap 64 or microcylinder 52 interface with the body 12 of the injector 10. Such sealing members 18 may include O-rings or any other suitable sealing device capable of reducing or eliminating the escape of pressurized gas. The injector 10 illustrated in FIG. 1 includes a sealing member 18 positioned such that, as the microcylinder 52 is mounted to the body 12 of the injector, a seal is formed between the body 12 of the injector 10 and the microcylinder 52 before the seal 58 of the microcylinder 52 is compromised. FIG. 5 and FIG. 6 illustrate injectors 10 of the present invention including a sealing member 18 positioned between the cap 64 and the body 12 of the injectors 10. The sealing member 18 is positioned within a seat 70 formed within the cap 64 and creates a seal that reduces or eliminates the escape of pressurized gas from the injector 10. Though the various figures providing illustrations of injectors of the present invention illustrate sealing members 18 at particular positions between the microcylinder 52, the cap 64, and the body 12 of the injector 10, the placement of sealing members 18 is not limited to the exact positions illustrated.

The actuator 100 of the injector 10 of the present invention may include any suitable mechanism capable of actuating the flow of pressurized gas from the pressurized gas source 50 to the driver 150 of the injector 10. For instance, where the injector 10 of the present invention includes a microcylinder 52 of compressed gas, the actuator 100 may include or trigger, piercing mechanism, plunger, or other force transfer mechanism that, upon actuation, compromises the microcylinder 52 (e.g., pierces, breaks, or penetrates the seal 58 or breaks away the elongated neck 62 of the microcylinder 52) and allows pressurized gas to escape to the driver 150 of the injector 10. Alternatively, where the design of the injector 10 does not require that the actuator 100 compromises the pressurized gas source 50, the actuator 100 may include a valve for actuating the flow of pressurized gas from the pressurized gas source 50 to the driver 150. In order to prevent accidental activation, or "firing," of the injector 10, the actuator 100 may also be linked to or protected by a safety mechanism that serves to prevent triggering of the actuator 100 until a deliberate act is executed in preparation for use of the injector 10.

FIG. 1 illustrates an injector 10 according to the present invention that includes an actuator 100 comprising a valve assembly 102 that allows the user to actuate flow of compressed gas from the pressurized gas source 50, through a first fluid path 16, and to the driver 150 of the injector 10. The valve assembly 102 includes a valve seat 104, a valve body 106, a button 108, and a biasing element 110, which may include a spring, a rubber bumper, a polymer bumper, or any other suitable resilient member. The biasing element 110 is placed within the valve seat 104 and acts against the valve body 106 to maintain valve body 106 in a normally closed position. In the closed position, the valve body 106 obstructs the first fluid path 16 and prevents gas flow to the driver 150. However, when sufficient pressure is exerted on the button 108, the valve body 104 is moved against the biasing member 110 into an open position (shown in FIG. 1). As the valve body 106 is placed in an open position, a depression 112 formed in the valve body 106 forms a second fluid path 114, which allows pressurized gas to flow from the first fluid path 16 to the driver 150. The valve body 106 may also include one or more sealing members 18, such as one or more O-rings. The sealing members 18 work to minimize any escape of pressurized gas from the valve assembly 102, particularly when the valve body 106 is placed in an open state.

As can be appreciated by reference to FIG. 1, where an injector 10 according to the present invention includes an actuator 100 comprising a valve assembly 102, the injector 10 may be provided with a mechanism designed to compromise the pressurized gas source 50 as it is mounted to the injector 10. The mechanism illustrated in FIG. 1 includes a hollow pierce pin 14, which defines a first fluid path 16 and penetrates the seal 58 of the microcylinder 52 as the cap 64 containing the microcylinder 52 is threaded onto the body 12 of the injector 10. In order to minimize the undesired escape of pressurized gas from the system, a sealing member 18, such as an O-ring, may be positioned between the microcylinder 52 and the body 12 of the injector 10 (shown in FIG. 1) or between the cap 64 and the body 12 of the injector 10. As the microcylinder 52 is secured to the injector 10, the sealing member 18 forms a seal between the microcylinder 52 and the body 12 of the injector 10 before the hollow pierce pin 14 has completely breached the seal 58 of the microcylinder 52. Once, the microcylinder 52 is secured to the injector 10 and the seal 58 of the microcylinder 52 is compromised, the flow of pressurized gas from the microcylinder 52 to the driver 150 is simply actuated through actuation of the valve assembly 102 of the actuator 100.

Figure 4:
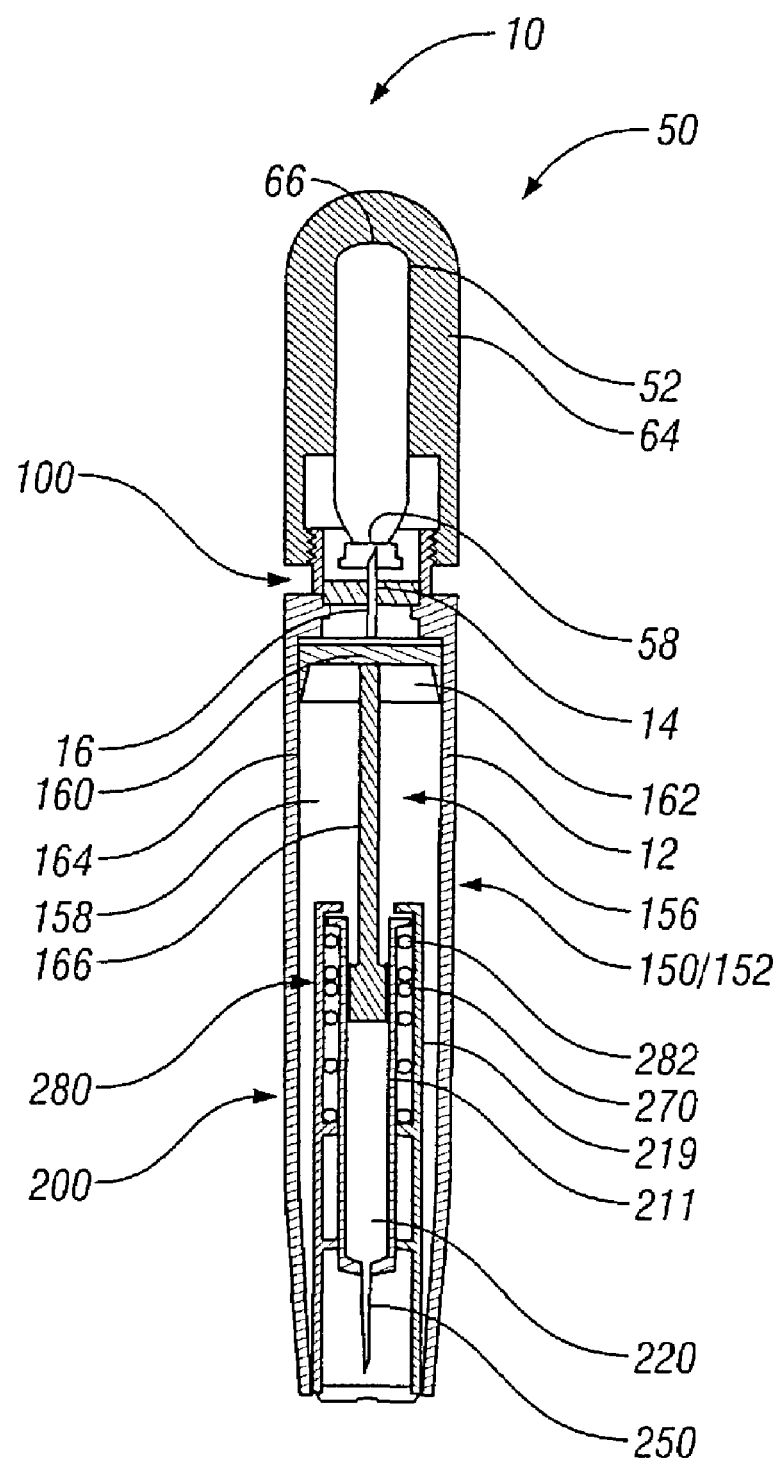
FIG. 4 illustrates an injector according to the present invention including a single stage driver and an actuator including a piercing mechanism.
Figure 7:
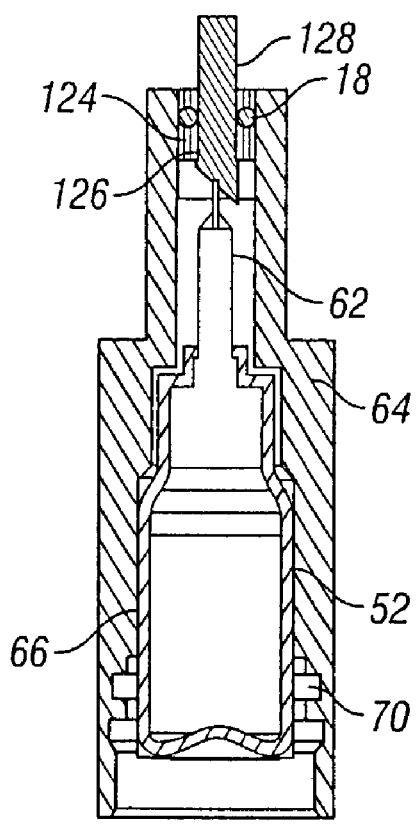
FIG. 7 and FIG. 8 illustrate caps that may be used in an injector of the present invention, the caps incorporating a plunger mechanism.
Figure 8:
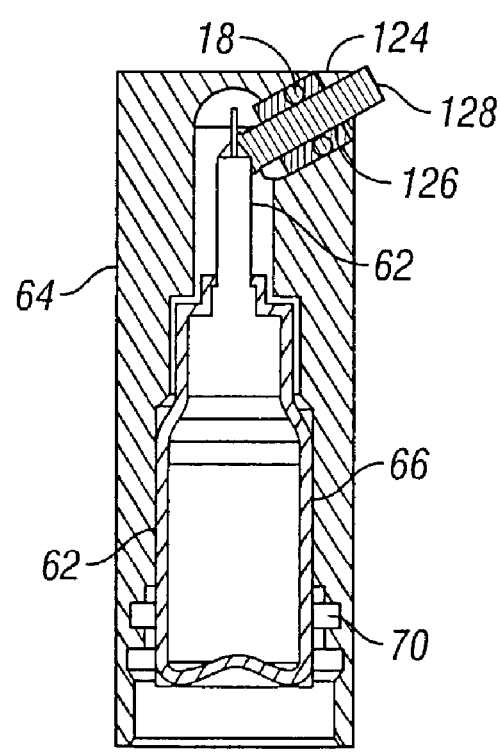

Instead of a valve assembly, the actuator 100 may simply include a piercing assembly, as is shown FIG. 4. Pressurized gas flow between the pressurized gas source 50 and the driver 150 of the injector 10 shown in FIG. 4 is actuated simply by mounting a cap 64 containing a microcylinder 52 to the body 12 of the injector. As the cap 64 containing the microcylinder 52 is mounted to the injector 10, a hollow pierce pin 14 compromises the seal 58 of the microcylinder 52 and pressurized gas is delivered to the driver 150 from the microcylinder 52 through the first fluid path 16.

Where a breakaway microcylinder 52 is used as the pressurized gas source 50 of an injector 10 according to the present invention, the actuator 100 of the injector 10 may include a plunger assembly 124, as shown in FIG. 6. The plunger assembly 124 may be incorporated into the body of the injector (not shown), or the plunger assembly 124 may be incorporated into a cap 64 containing the microcylinder 52 (shown in FIG. 6). Regardless of where it is provided, the plunger assembly 124 includes a passageway 126 within which the plunger 128 is disposed. The plunger assembly 124 may further include one or more sealing members 18, which form a seal between the plunger 128 and the passageway 126 and minimize the undesired escape of pressurized gas through the plunger assembly 124 during use of the injector 10. The plunger 128 may be moved back and forth within the passageway 126 and may be maintained within the passageway 126 of the actuator plunger mechanism 124 simply through a friction-fit or any other suitable means. Whether it is included in the body 12 of the injector 10 or a cap 64 containing the microcylinder 52, the plunger assembly 124 is positioned such that the depression of the plunger 128 with sufficient force will break away the elongated neck 62 of the microcylinder 52. Though the plunger 128 of the plunger assembly 124 illustrated in FIG. 6 is positioned generally perpendicularly to the longitudinal axis of the microcylinder 52 contained within the cap 64, such a configuration is not required, as shown in FIG. 7 and FIG. 8.

The injector illustrated in FIG. 6 includes a safety mechanism 20, which serves to minimize accidental activation of the injector 10. The safety mechanism 20 includes a first portion 22, a second portion 24, and a spring 26. The first portion 22 is generally cylindrical in shape and includes a stop 32 and a slot 30 terminating in a port 31. The second portion 24 of the safety mechanism 20 is also generally cylindrical in shape. At its distal end 34, the second portion 24 includes a lip 36 sized to allow the passage of the adjustable tip 230 of the dispenser 200, but the lip 36 also serves as a mechanical stop, preventing the passage of the body 12 of the injector 10 through the distal end 34 of the second portion 24. The spring 26 is positioned within a seat 38 formed in the body 12 of the injector 10, and after the spring 26 is positioned within the seat 38, the first and second portions 22, 24 of the safety mechanism 20 are fastened together by any suitable means. For example, the first and second portions 22, 24 may be bonded, welded, glued, threaded, or snap-fit together. The spring 26 acts against the distal end 40 of the first portion 22 to bias the safety mechanism in a "safe" position. In the safe position, the stop 32 included on the first portion 22 prevents actuation of the actuator 100 included in the injector 10.

The safety mechanism is moved out of the safe position illustrated in FIG. 6 by sliding the first and second portions 22, 24 against the spring 26 such that the stop 32 no longer interferes with the actuator 100. This may be accomplished by positioning the injector 10 generally perpendicularly against the tissue of a subject and applying a downward force sufficient to overcome the bias force exerted by the spring 26 of the safety mechanism 20. In the example shown in FIG. 7, the neck 129 of the plunger 128 passes through the slot 30 as the first and second portions 22, 24 are slid against the spring 26. Preferably, however, the slot 30 is sized to prevent the body 130 of the plunger 128 from being expelled from the passageway 126 as pressurized gas is released from the microcylinder 52.

Figure 23:
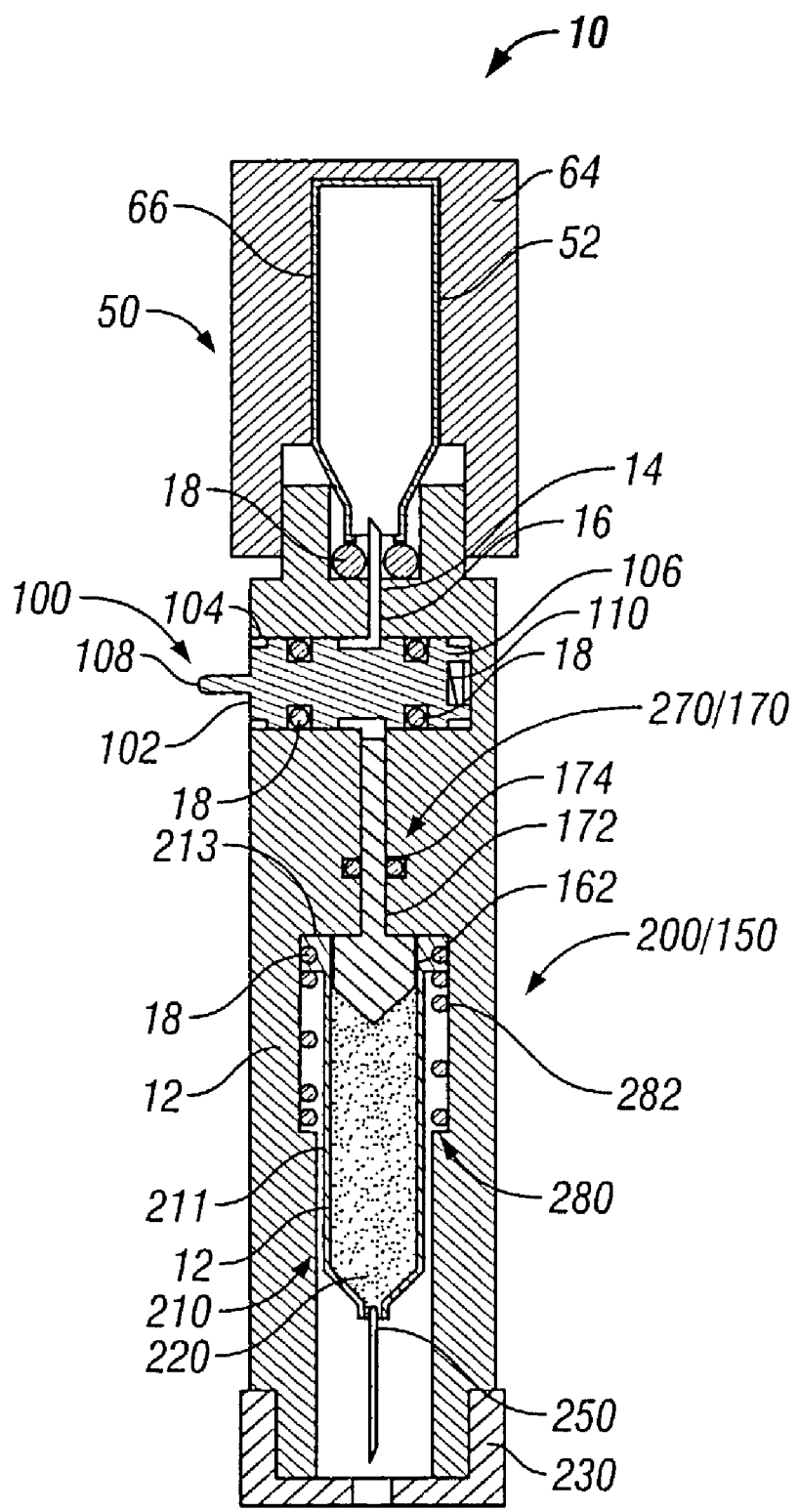
FIG. 23 illustrates an injector of the present invention that includes an integrated driver and dispenser including a multistage piston.
Figure 24:
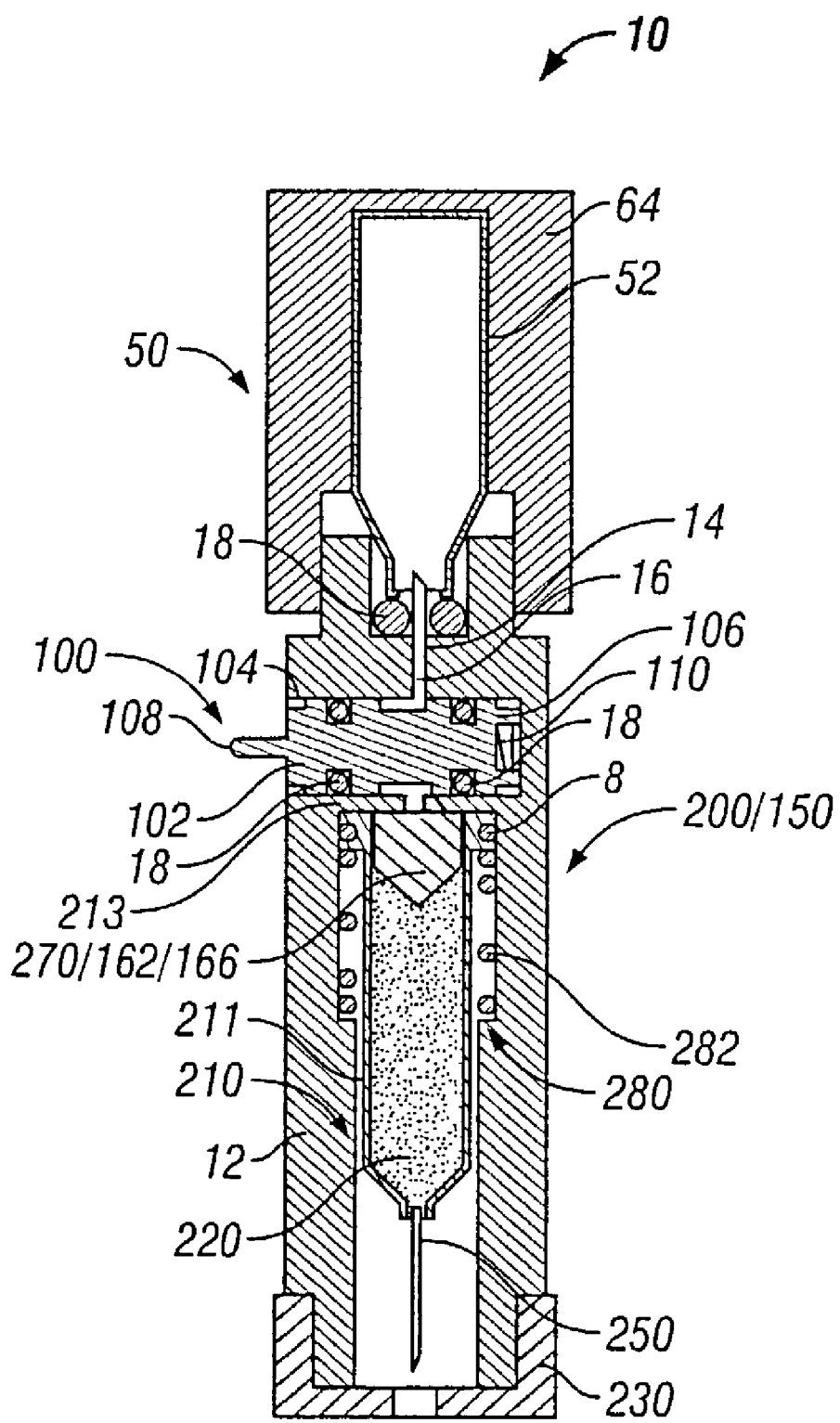
FIG. 24 illustrates an injector of the present invention that includes an integrated driver and dispenser including a single stage piston.

The driver 150 of the present invention may be designed as a single stage driver 152 or a multistage driver 154. FIG. 4 and FIG. 24 illustrate injectors 10 according to the present invention including a single stage driver 152, while FIG. 1, FIG. 5, FIG. 6, FIG. 9, FIG. 10, and FIG. 23 illustrate injectors 10 according to the present invention including a multistage driver 154.

Where the driver 150 of the present invention is a single stage driver 152, the single stage driver 152 includes a single stage piston 156 disposed within a pneumatic cylinder 158 having at least one chamber 160. The single stage piston 156 provided in the single stage driver 152 includes a injection stage 162 and may include a sealing member, such as an O-ring or cup seal (not shown in FIG. 4), that forms a seal between the injection stage 162 and the wall 164 of the chamber 160 of the pneumatic cylinder 158. The single stage piston 156 optionally includes a plunger 166, which extends out and away from the injection stage 162 and is positioned to act against the dispenser 200 as the single stage piston 156 is driven through its stroke within the pneumatic cylinder 158.

As pressurized gas enters the pneumatic cylinder 158 of a single stage driver 152, the pressurized gas acts against the injection stage 162 and drives the single stage piston 156 through its stroke with an injection force. The magnitude of the injection force exerted by the single stage piston 156 is equal to the surface area of the injection stage 162 multiplied by the pressure created within the chamber 160 of the pneumatic cylinder 158 (Force=Pressure×Area). Therefore, where a given pressure or pressure profile is produced within the chamber 160 of the pneumatic cylinder 158, the magnitude of the injection force exerted by the single stage piston 156 may be adjusted, as desired, by increasing or decreasing the surface area of the injection stage 162. The injection stage 162 of the single stage piston 154 is sized to ensure that the single stage piston 156 exerts an injection force sufficient to deliver a desired dose of a chosen medicament within a desired amount of time.

A multistage driver 154 included in an injector 10 according to the present invention includes a pneumatic cylinder 158 having at least two chambers 167, 168 and a multistage piston 170 having at least an insertion stage 172 and an injection stage 162. The insertion stage 172 of the multistage piston 170 is characterized by a first surface area and may include a first sealing member 174, such as an O-Ring. Alternatively, the first sealing member 174 may be provided in a seat 176 created within the wall 178 of the first chamber 167. The injection stage 162 of the multistage piston 170 is characterized by a second surface area, which is larger than the first surface area of the insertion stage 172. The injection stage 162 may include a second sealing member 180, such as an O-ring or cup seal, which creates a seal between the wall 182 of the second chamber 168 and the injection stage 162 as the multistage piston 170 is driven through its stroke. The multistage piston 170 may also a plunger 166 that extends out and away from the injection stage 162 and is positioned to act against the dispenser 200 of the injector 10. The pneumatic cylinder 158 and the multistage piston 170 are designed such that pressurized gas entering the pneumatic cylinder 158 acts against the insertion stage 172 and the injection stage 162 sequentially, thereby causing the multistage piston 170 to sequentially exert at least an insertion force and an injection force.

Pressurized gas entering a multistage driver 154 included in an injector of the present invention acts sequentially against each stage. For example, pressurized gas entering the multistage driver 154 illustrated in FIG. 1, FIG. 5, FIG. 6, FIG. 9, FIG. 10, FIG. 23 acts first against the insertion stage 172 and second against the injection stage 162 of the multistage piston 170. As pressurized gas acts against the insertion stage 172, the multistage piston 170 exerts an insertion force. The magnitude of the insertion force is equal to the pressure produced within the first chamber 167 of the pneumatic cylinder 158 multiplied by the surface area of the insertion stage 172 (Force=Pressure×Area). Therefore, where a given pressure or pressure profile is produced within the first chamber 167, the insertion force exerted by the multistage piston 170 may be increased or decreased as desired simply by increasing or decreasing the surface area of the insertion stage 172. Advantageously, the insertion stage 172 of a multistage piston 170 may be sized such that the multistage piston 170 exerts an insertion force that minimizes subject discomfort.

Once the insertion stage 172 of the multistage piston 170 is driven through a predetermined stroke, pressurized gas enters the second chamber 168 of the pneumatic cylinder 158 and acts against the injection stage 162, causing the multistage piston 170 to exert an injection force. The injection force exerted by the multistage piston 170 is equal to the pressure generated within the second chamber 168 multiplied by the surface area of the injection stage 162. Therefore, where a given pressure or pressure profile is produced within the second chamber 168, the magnitude of the injection force exerted by the multistage piston 170 may be increased or decreased, as desired, by increasing or decreasing the surface area of the injection stage 162. Again, the injection stage 162 is sized to ensure the production of an injection force sufficient to deliver a desired dose of a chosen medicament within a desired amount of time.

Achieving a desired pressure or pressure profile within the driver of an injector of the present invention may be accomplished by altering one or more of several design variables. For example, if the injector of the present invention does not include a pressure regulator or a restrictor, the pressure produced within driver will depend on the pressure and volume of compressed gas contained within the pressurized gas source, the volume of the pneumatic cylinder, and the stroke of the piston included in the pneumatic cylinder. If the injector includes a restrictor, the pressure generated within the driver will depend upon the pressure and volume of compressed gas contained within the pressurized gas source, the maximum rate of gas flow permitted by the restrictor, and the rate at which the medicament flows from the dispenser once a suitable injection force is generated. Finally, where the injector of the present invention includes a pressure regulator, the pressure generated within the driver can be controlled independently of the volume of the pneumatic cylinder, the stroke of the piston, or the rate at which medicament flows from the dispenser. Therefore, to create a desired pressure, series of pressures, or pressure profile within the driver of the injector of the present invention, any one of several components can be adjusted or added.

FIG. 1, FIG. 2, FIG. 5, FIG. 6, FIG. 23, and FIG. 24 illustrate injectors 10 according to the present invention that do not include either a restrictor or a pressure regulator. The pressure generated within the pneumatic cylinder 158 of the driver 150 of such injectors 10 can be accurately predicted and adjusted using the Ideal Gas Law, $P_1 V_1 = P_2 V_2$. If the volume and pressure of the pressurized gas source 50 are taken to be $P_1$ and $V_1$, respectively, and the volume of the pneumatic cylinder 158 is taken to be $V_2$, then the pressure ($P_2$) generated within the pneumatic cylinder equals 158 the product of $P_1$ and $V_1$ divided by $V_2$. Therefore, the pressure generated within the pneumatic cylinder 158, is directly proportional to volume and pressure of the gas contained within the pressurized gas source 50 and inversely proportional to the volume of the pneumatic cylinder 158. Using this relationship, the pressure generated within the pneumatic cylinder 158 of an injector 10 lacking both a restrictor and a pressure regulator can be adjusted to a desired magnitude simply by modifying the pressure of the gas contained within the pressurized gas source 50 or by modifying the volume of either the pressurized gas source 50 or the pneumatic cylinder 158.

As can be easily appreciated, where the injector 10 of the present invention does not include either a restrictor or a pressure regulator, the pressure produced in the one or more chambers 160, 167, 168 of the pneumatic cylinder 158 will decrease at least slightly as the piston 156, 170 moves through its stroke. This is because the pressure ($P_2$) generated within pneumatic cylinder 158 is inversely proportional to the volume ($V_2$) filled by the pressurized gas, and as the piston 156, 170 moves through its stroke the volume ($V_2$) filled by pressurized gas necessarily increases. However, the extent to which the pressure ($P_2$) decreases within the one or more chambers 160, 167, 168 of the pneumatic cylinder 158 can be at least partially controlled by varying the pressure ($P_1$) and volume ($V_1$) of gas contained in the pressurized gas source 50 or by increasing or decreasing the stroke of the piston 156, 170, which will increase or decrease the change in volume ($V_2$) as the piston 156, 170 is driven through the pneumatic cylinder 158. For example, for a pneumatic cylinder 158 of a given volume, the drop in pressure will be attenuated as the volume or pressure of gas delivered by the pressurized gas source 50 increases. Conversely, the drop in pressure within a pneumatic cylinder 158 of a given volume will be accentuated as the pressure or volume of gas delivered by the pressurized gas source 50 is decreased. Therefore, even where the injector 10 of the present invention does not include a restrictor or a pressure regulator, the range of insertion or injection forces produced by the driver 150 of the injector 10 may be controlled by controlling the volume of the pneumatic cylinder 158, the dimensions of each stage 162, 172 of the piston 156, 170, and the volume and pressure of pressurized gas stored within the pressurized gas source 52.

Figure 9:
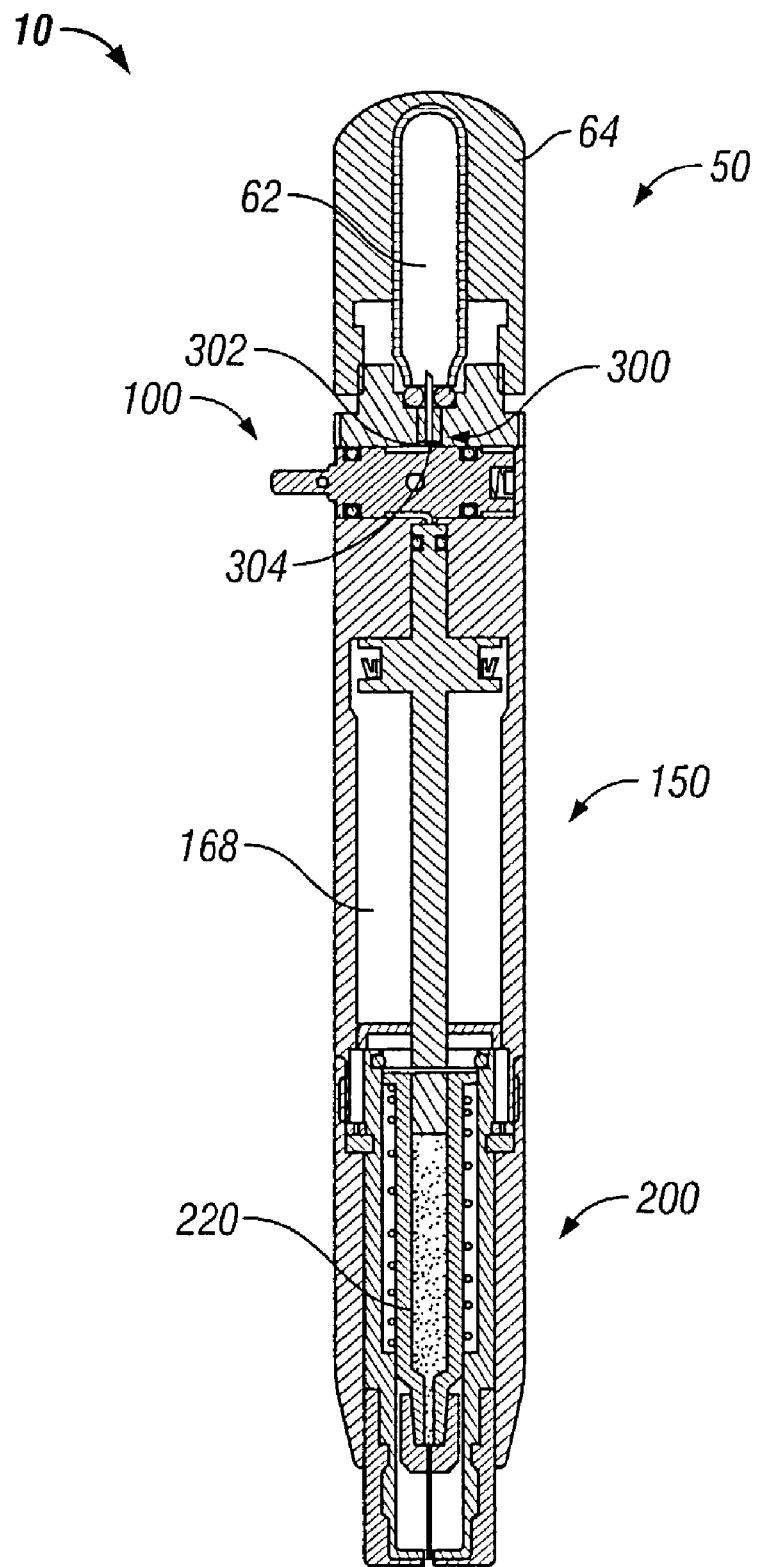
FIG. 9 illustrates an injector according to the present invention that incorporates a restrictor.
Figure 11:
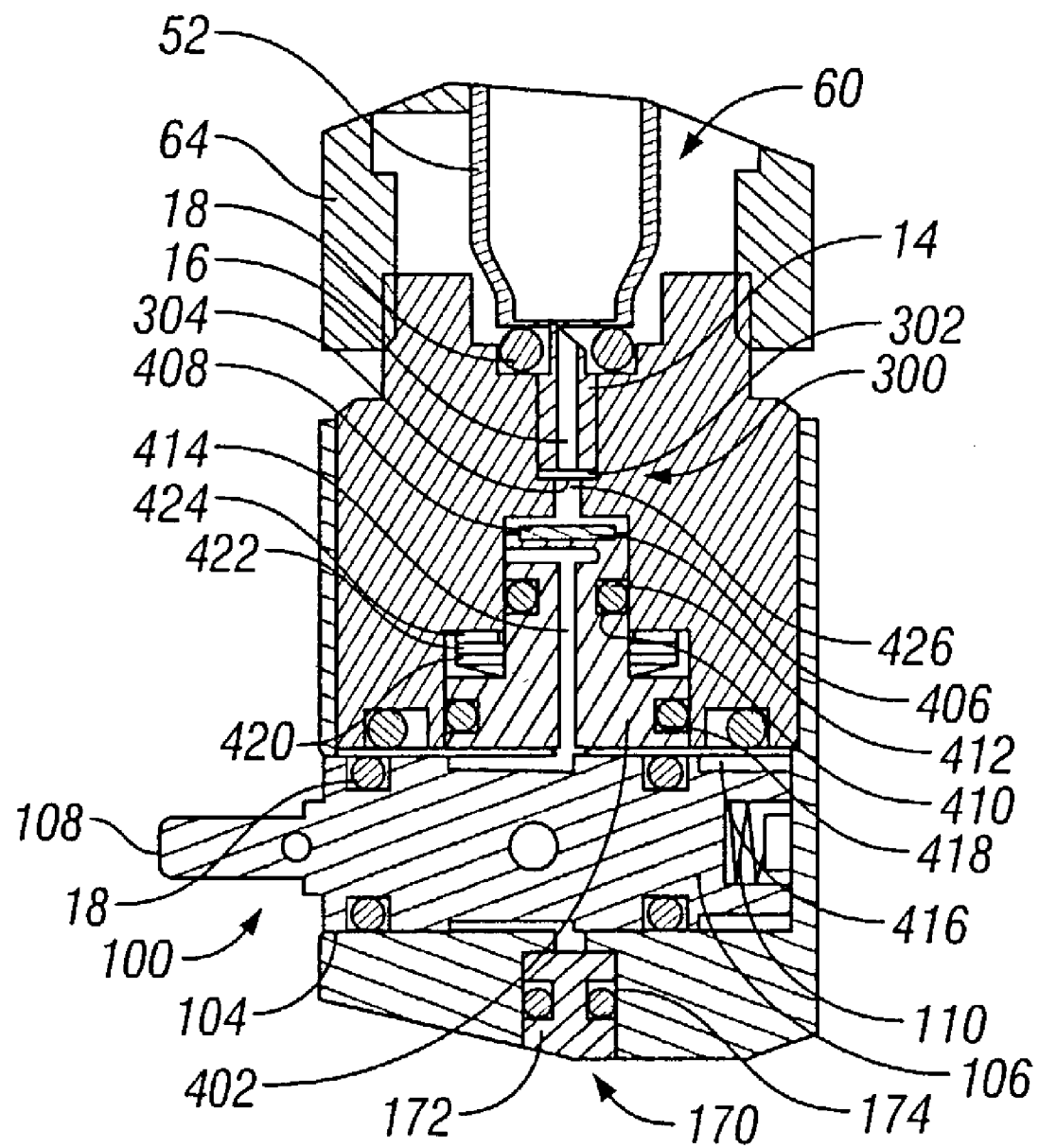
FIG. 11 through FIG. 13 illustrate the pressure regulator provided in the injectors illustrated in FIGS. 10a and 10b.
Figure 12:
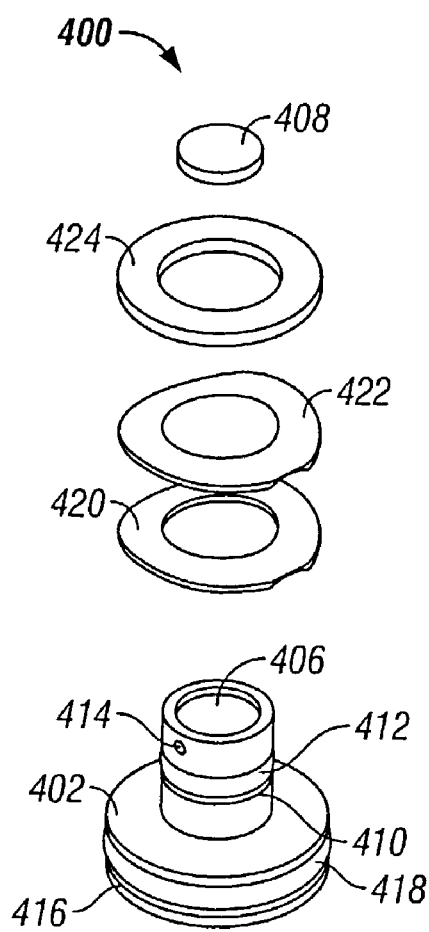
Figure 13:
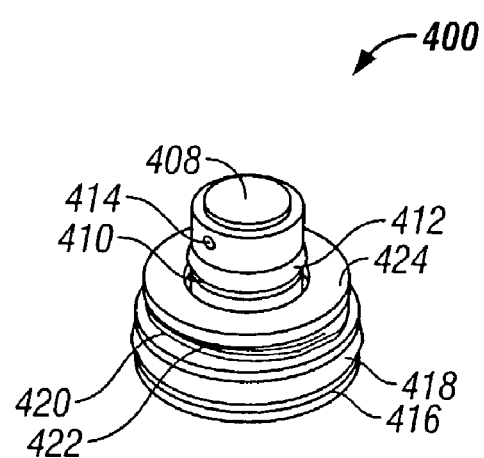

If greater control of the pressure produced within the driver 150 is desired, the injector 10 of the present invention may be provided with a restrictor 300 or a pressure regulator 400. FIG. 9 illustrates an injector 10 according to the present invention including a restrictor 300, while FIG. 10 illustrates an injector 10 according to the present invention, which include a pressure regulator 400. By providing the injector 10 of the present invention with a restrictor 300 or a pressure regulator 400, a substantially constant gas pressure can be produced within the pneumatic cylinder 158 of the driver 150, thereby producing substantially constant insertion or injection forces.

As can be appreciated by reference to FIG. 9, where a restrictor 300 is included in the injector 10 of the present invention, the restrictor 300 may simply include a plate 302 having an orifice 304 sized as desired to limit gas flow to a targeted maximum rate. The flow rate allowed by such a restrictor 300 is easily increased or decreased by increasing or decreasing the size of the orifice 304 included in the plate 302. Alternatively, the injector 10 may include an adjustable restrictor (not shown) that allows the user to select a desired rate of gas flow within a given range. For instance, an adjustable restrictor may include a screw mechanism that is advanced or retracted as desired within a fluid passageway. As the screw mechanism is advanced within the fluid passageway, the fluid passageway is contracted and allows a relatively smaller maximum gas flow. As the screw mechanism is retracted, however, the fluid passageway is expanded, allowing a relatively larger maximum gas flow. Though the restrictor 300 shown in FIG. 9 is positioned between the actuator 100 and the pressurized gas source 50 of the injector 10, a restrictor 300 included in an injector 10 of the present invention can be positioned in any other suitable location, such as between the actuator 100 and the pneumatic cylinder 158 of the driver 150.

By adjusting the maximum gas flow allowed by the restrictor 300, the injector 10 of the present invention may be designed to provide a substantially constant injection force. In order to achieve a substantially constant injection force through use of a restrictor 300, the maximum rate of gas flow permitted by the restrictor 300 is tuned to match the rate at which medicament 220 is expelled from the dispenser 200 once an injection force is created within the pneumatic cylinder 158 of the driver 150. If the maximum rate of gas flow allowed by the restrictor 300 is tuned to match the rate at which the medicament 220 is expelled from the dispenser 200, the pressure within the pneumatic cylinder 158 will remain substantially constant as the medicament 220 is delivered to the subject. Therefore, the injector 10 of the present invention can be designed to exert a substantially constant injection force simply by providing the injector 10 with a properly tuned restrictor 300.

FIG. 10a through FIG. 13 illustrate an exemplary pressure regulator 400, which allows constant insertion and injection forces to be produced independently of the volume of the pneumatic cylinder 158 included in the driver 150, the stroke of the piston 170, or the rate at which medicament 220 is expelled from the dispenser 200. The pressure regulator 400 illustrated in these figures includes a base 402 and a cylindrical protrusion 404 extending out from the base 402. The cylindrical protrusion 404 includes a first seat 406 for a first sealing element 408, a second seat 410 for a second sealing element 412, and a first fluid path 414. The first fluid path 414 facilitates flow of compressed gas from the pressurized gas source 50 to the actuator 100. The base 402 includes third seat 416 for a third sealing element 418 and serves as a platform for a first spring element 420, a second spring element 422, and a spacer ring 424. The first and second spring elements 420, 422 are positioned over the base 402 and around the cylindrical protrusion 404, and the spacer ring 424 is positioned over the first and second springs elements 420, 422. The sealing members 408, 412, 418 included in the pressure regulator may include any suitable sealing element, such as a gasket or an O-ring seal. Though any suitable structure may be used to create a pressure regulator 400 useful in the injector of the present invention, the pressure regulator 400 illustrated in FIG. 10a through FIG. 13 provides a compact device capable of maintaining the pressure within the driver 150 at or below a predetermined level.

In use, pressurized gas passes from the pressurized gas source 50, through the first fluid path 414 of the pressure regulator 400, and to the driver 150. As it flows to the driver 150 and accumulates, the pressurized gas exerts pressure against the base 402 of the pressure regulator 400. The pressure acting against the base 402 causes the base 402 to exert a force against the first and second spring elements 420, 422, and as the pressure within the system approaches a predetermined threshold, the force exerted by the base 402 begins to compress the first and second spring elements 420, 422. This pushes the first seal 408 closer to an aperture 426, thereby restricting flow of pressurized gas from the pressurized gas source through the aperture 426. If the pressure acting against the base 402 reaches or exceeds the predetermined threshold, the force exerted by the base 402 overcomes the first and second spring elements 420, 422 and the first seal 408 of the pressure regulator 402 seals the aperture 426, terminating gas flow from the pressurized gas source 50. As the pressure decreases below the predetermined threshold, the force exerted by the base 402 decreases and the first and second spring elements 420, 422 draw the first seal 408 away from the aperture 426, allowing pressurized gas to flow from the pressurized gas source 50 once again.

The threshold pressure of the pressure regulator 400 shown in FIG. 10a through FIG. 13 is easily set to any desired value. The maximum pressure that is allowed by the pressure regulator 400 is determined by the surface area of the base 402 and the combined bias force exerted by the first and second spring elements 420, 422. For example, a pressure regulator designed to maintain the pressure within the driver at or below about 100 psi may be designed by providing a base 402 having a diameter of about 0.5 inches and first and second spring elements 420, 422 that exert a combined maximum spring force of 20 lbs. As a pressure within the driver 150 reaches or exceeds about 100 psi, the force exerted by the base 402 against the first and second spring elements 420, 422 will reach or exceed 20 lbs. (Force=Pressure×Area), causing the first seal 408 to seal the aperture 426 and terminate gas flow into the driver 150. By increasing or decreasing either the surface area of the base 402 or the combined bias force exerted by the first and second spring elements 420, 422, a pressure regulator 400 may be designed to maintain virtually any desired maximum pressure within the driver 150.

As can be seen in FIG. 10*b*, the injector 10 of the present invention is not limited to including only a pressure regulator 400 or only a restrictor 300. If desirable or necessary, the injector 10 of the present invention may include both a pressure regulator 400 and a restrictor 300. Further, as is appreciable by reference to FIG. 10*a* and FIG. 10*b*, where the injector 10 of the present invention is provided with a pressure regulator 400, the pressure regulator 400 may be contained within a housing 430. Such a housing 430 is designed to received within the body 12 of the injector 10, and the housing 430 may be mounted to the body 12 using any suitable means. For example, the housing 430 may include a first threaded area complimentary to a second threaded area provided on the body 12 of the injector 10. Alternatively, the housing 430 may be mounted to the body 12 using any suitable adhesive or bonding methods. Though the pressure regulator 400 need not be provided in a housing 430 separate from the body 12 of the injector 10, providing a housing 430 for the pressure regulator may ease the manufacture of the body 12 and may simplify the inclusion of a pressure regulator 400 in an injector 10 of the present invention.

Just as the use of a housing 430 for the pressure regulator 400 may simplify inclusion of a pressure regulator 400 in the injector 10 of the present invention, providing an injector 10 of the present invention with a multi-piece body 12 may ease fabrication of the injector 10. For instance, the body 12 of the injectors 10 illustrated in FIG. 5 and FIG. 6 is constructed of a proximal portion 40 and a distal portion 42. The proximal and distal portions 40, 42 are joined at an interface 44, for example, by a threading mechanism, a suitable adhesive, bonding, or welding process, or any other known means providing secure attachment. A sealing member 18, such as an O-ring, may be provided at the interface 44 of the proximal and distal portions 40, 42 in order to reduce or eliminate the unwanted escape of pressurized gas from the injector 10. Both the proximal portion 40 and the distal portion 42 are designed with various features that facilitate the assembly and proper function of the injector 10, and by manufacturing the proximal and distal portions 40, 42 as different pieces, the design and creation of the various features of each portion may be eased. For example, if the proximal and distal portions 40, 42 of the body 12 of the injectors illustrated in FIG. 5 and FIG. 6 were integrated into a one-piece body, the creation of the seat 176 for the first sealing member 174 would be relatively difficult, possibly requiring custom tooling and likely increasing the cost of fabricating the injector 10 of the present invention. However, because the proximal portion 40 of the injectors 10 illustrated in FIG. 5 and FIG. 6 is manufactured separately from the distal portion 42, the seat 176 for the first sealing member 174 is easily and inexpensively created within the proximal portion 40 before the proximal portion 40 and the distal portion 42 are joined to form the body 12 of the injector 10. Therefore, though it is not required, the body 12 of the injector 10 of the present invention may be manufactured in multiple components to facilitate the manufacture or fabrication of the injector 10.

As is true of the components already discussed, the design of the dispenser 200 of the injector 10 of the present invention is flexible. The dispenser 200 of the injector 10 need only include a reservoir 210, such as a syringe 211, suitable to contain a desired viscous medicament 220, a needle 250 of suitable gauge to deliver the desired medicament 220 to the subject, and a piston 270 to drive the medicament from the reservoir 210 through the needle 250. Though the injectors 10 illustrated herein include a dispenser 200 including a piston 270 that is separate from the single stage or multistage pistons 156, 170 included in the driver 150 of those injectors 10, the piston 270 of the dispenser 200 may also be integrated into the plunger 166 of the piston 156, 170 included in the driver 150.

The gauge of the needle 250 included in the dispenser 200 is generally chosen to be as small as practical. Although the force and time required to deliver a given medicament 220 through the needle 250 will generally increase as the diameter of the needle 250 decreases, subject comfort generally increases as the diameter of the needle 250 decreases. As a result, particularly where the intended subject is human, the gauge of the needle 250 included in the dispenser is preferably ranges from 21 gauge to 31 gauge. Even more preferably, the needle 250 included in the dispenser will have a gauge ranging between 24 gauge and 31 gauge, and most preferably, the needle 250 will have a falling within the range of 27 gauge to 31 gauge. Though a smaller gauge needle will generally be preferred over a larger gauge needle, where the difference in gauge would not significantly alter the comfort of the subject, the larger gauge needle may be chosen to decrease the injection force or injection time required to deliver a given medicament. Further, although 21 gauge to 31 gauge needles are presently preferred, where desired or necessary, the injector of the present invention can be provided with a needle having a gauge outside that presently preferred range.

To the extent possible, the inner diameter $D_R$ of the reservoir 210 should be chosen to approximate the gauge of the needle 250. This is because the injection force required to drive a viscous medicament from the reservoir 210 through the needle 250 increases exponentially as the inner diameter $D_R$ of the reservoir 210 increases away from the inner diameter $D_N$ of the needle 250. Of course, the benefits of approximating the inner diameter $D_R$ of the reservoir 210 to the inner diameter $D_N$ of the needle 250 are balanced against other design factors, such as the desired size of the dispenser 200 and the volume of medicament 220 to be delivered.

The dispenser 200 may also include a bias mechanism 280, whereby the needle 250 and reservoir 210 of the dispenser 200 are maintained in a retracted position until an insertion or injection force is communicated to the dispenser 200 from the driver 150. Where the driver 150 of the injector 10 includes a single stage piston 156, the bias mechanism 280 retains the reservoir 210 and needle 250 in a retracted position until an injection force is exerted against the piston 270 of the dispenser. However, where the driver 150 of the injector 10 includes a multistage piston 170, the bias mechanism 280 maintains the needle 250 and reservoir 210 in a retracted position until an insertion force is exerted against the piston 270 of the dispenser. Moreover, regardless of whether the injector 10 includes a multistage driver 154 or single stage driver 152, as the pressure created within the injector 10 dissipates after an injection cycle, the bias mechanism 280 automatically retracts the reservoir 210 and needle 250 within the dispenser 200.

The bias mechanism 280 may include any suitable device for biasing the reservoir 210 and needle 250 in a retracted position. For example, the bias mechanism 280 may include a coil spring 282 supporting the reservoir 210 and needle 250 within the dispenser 200. Alternatively, the bias mechanism 280 may include any other suitable biasing member, such as a solid or foamed rubber or polymer bumper, or a fluid filled, resilient bladder. The spring rate or force required to compress the bias mechanism 280 may be varied, as desired, provided that such spring rate or force is at least sufficient to bias the reservoir 210 and needle 250 in a retracted position.

Where an injector 10 of the present invention includes a single stage driver 152 and a bias mechanism 280, the injection force exerted by the single stage driver 152 and the bias force exerted by the bias mechanism 280 may be adjusted to provide an effective insertion force of desired magnitude. The effective insertion force is the force with which the needle 250 extends from the casing 219 of the dispenser, and where the injector 10 of the present invention includes a single stage driver 150 and a bias mechanism 280, the effective insertion force is equal to the injection force generated by the single stage driver 152 minus the bias force exerted by the bias mechanism 280. By adjusting either the injection force exerted by the single stage driver 152 or the bias force exerted by the bias mechanism 280, a desired effective insertion force may be achieved. For instance, where an injection force of 10 lbs. is required, an effective insertion force of about 1 lbs. to about 7 lbs. may be achieved by providing a bias mechanism 280 that exerts a bias force of about 9 lbs. to about 3 lbs. Even if higher injection forces are necessary, an effective insertion force of about 1 lbs. to about 7 lbs. may be achieved by providing a bias mechanism 280 capable of exerting a higher bias force. Therefore, even where the injector 10 of the present invention includes a single stage driver 152, the injector 10 may be designed to provide an effective insertion force tailored to minimize subject discomfort, while simultaneously generating an injection force sufficient to deliver a chosen medicament within a desired amount of time.

The effective insertion force of an injector 10 including a multistage driver 154 and a bias mechanism 280 may also be adjusted as desired. Where the injector 10 of the present invention includes a multistage driver 154 and a bias mechanism 280, the effective insertion force is equal to the insertion force exerted by the multistage driver 154 minus the bias force exerted by the bias mechanism 280. Consequently, the effective insertion force provided by an injector 10 including a multistage driver 154 and a bias mechanism 280 is easily adjusted by altering either the insertion force exerted by the multistage driver 154 or the bias force exerted by the bias mechanism 280. For example, where the bias mechanism 280 exerts a bias force of about 1 lbs. and an effective insertion force of about 1 lbs. to 7 lbs. is desired, the pressurized gas source 50 and the multistage driver 154 of the injector 10 may be designed to exert an insertion force of about 2 lbs. to 8 lbs. Alternatively, if the pressurized gas source 50 and multistage driver 154 of the injector 10 are designed to exert an insertion force of about 5 lbs. and an effective insertion force of about 1 lbs. to about 4 lbs. is desired, the dispenser 200 of the injector 10 may be provided with a bias mechanism 280 exerting a bias force of about 1 lbs. to 4 lbs. Thus, where the injector 10 of the present invention includes both a bias mechanism 280 and a multistage driver 154, the effective insertion force provided by the injector 10 can be tailored, as desired, to minimize subject discomfort.

A range of about 1 lbs. to about 7 lbs. is specifically discussed in relation to injectors 10 of the present invention including multistage and single stage drivers 152, 154, because it is thought that, where a needle having a gauge ranging from 21 gauge to 31 gauge is used, an effective insertion force of between about 1 lbs. and 7 lbs. will minimize subject discomfort. However, the injector 10 of the present invention is not limited to those designs providing an effective insertion force ranging from about 1 lbs. to about 7 lbs. The design of the injector 10 of the present invention is highly flexible, and the injector 10 of the present invention may be designed to insert the needle 250 included in the dispenser 200 with virtually any desired force.

Figure 14:
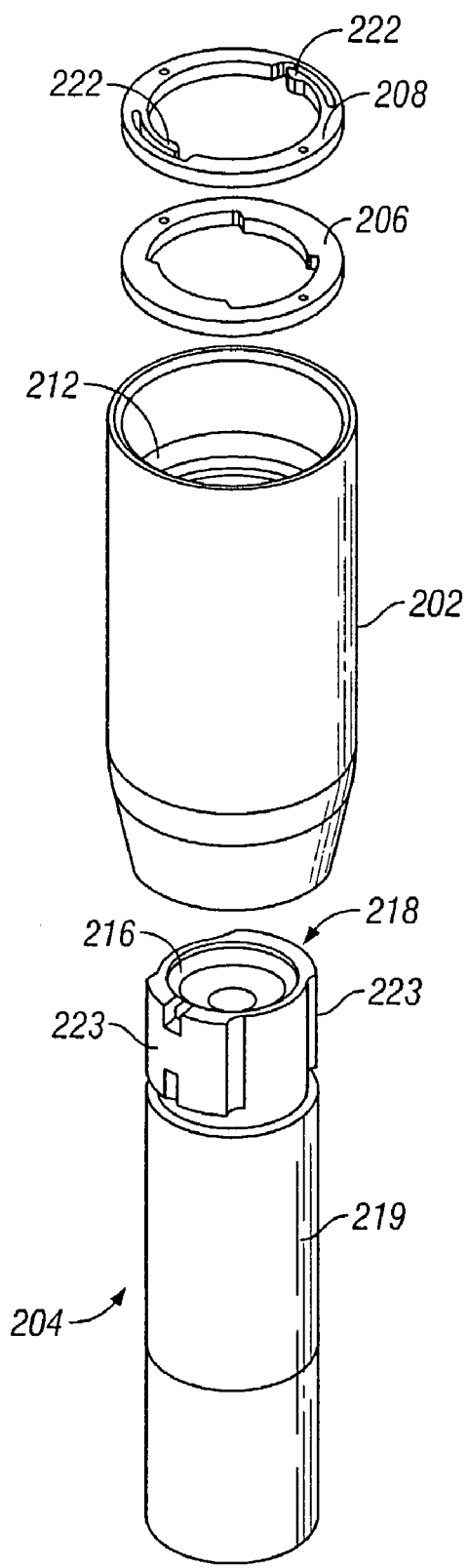
FIG. 14 and FIG. 15 illustrate a syringe cartridge that may be used as a dispenser for an injector of the present invention.
Figure 15:
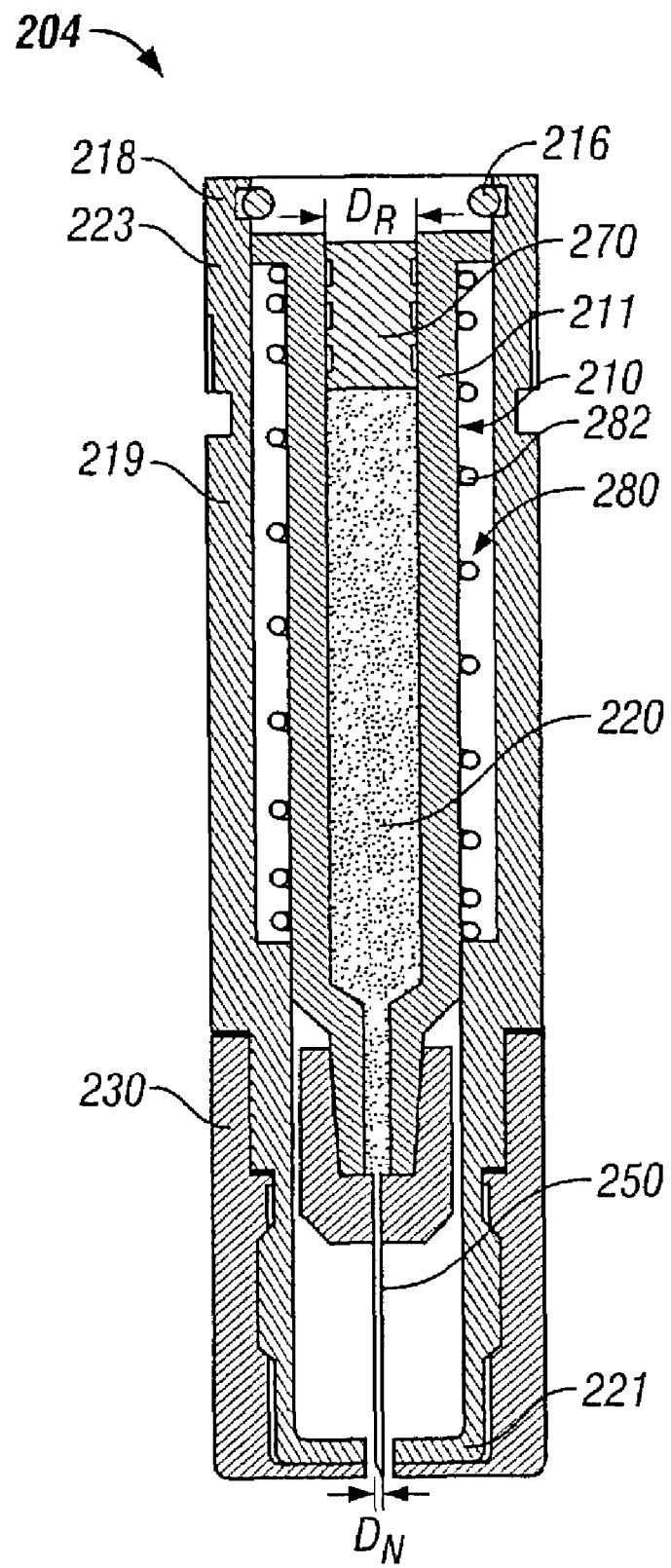
Figures 16, 17:
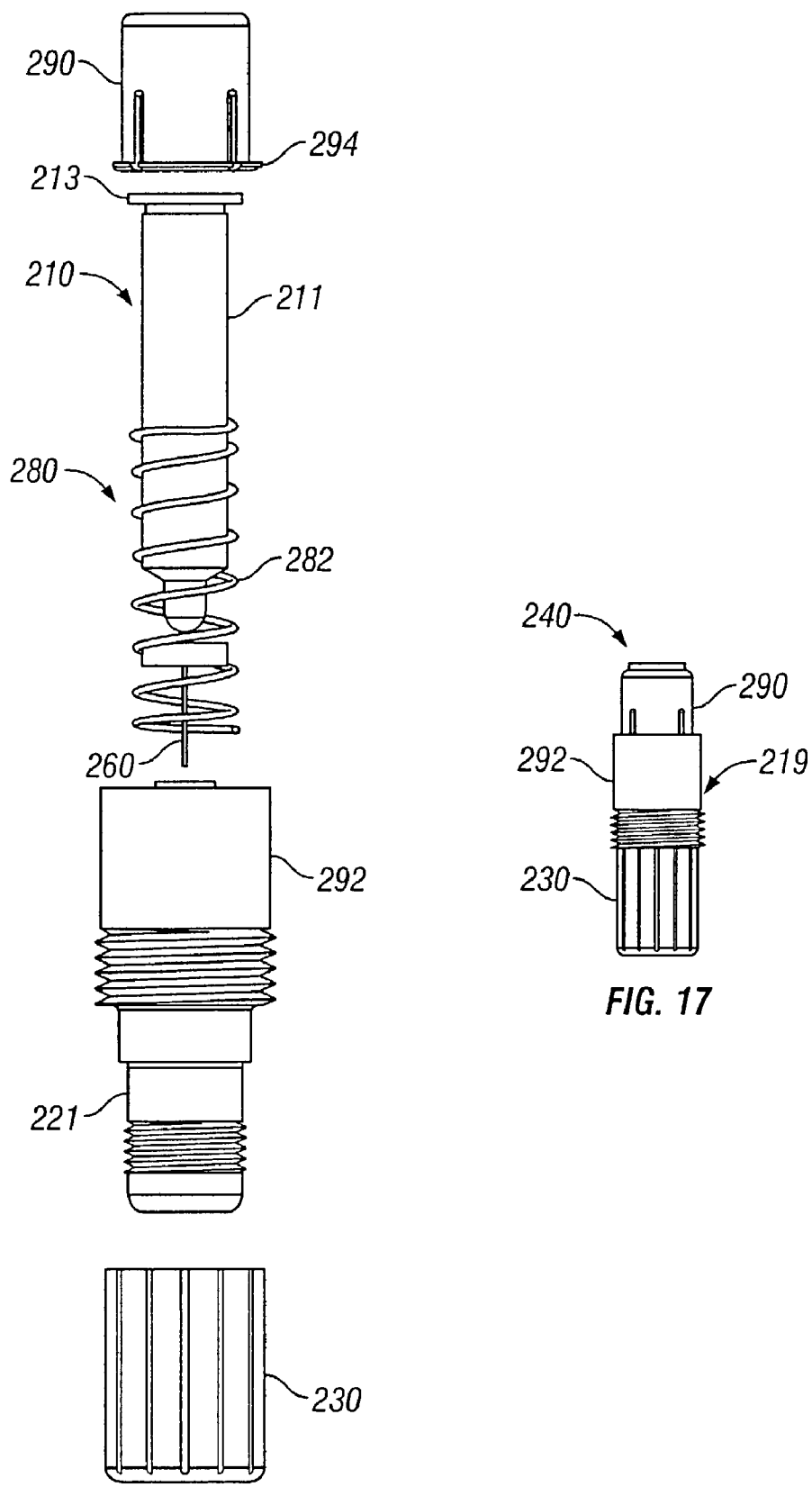

FIG. 14 through FIG. 15 illustrate a first syringe cartridge 204 that may be used as a dispenser 200 in an injector 10 according to the present invention (See FIG. 1, FIG. 9 and FIG. 10). As can be seen in FIG. 14, the dispenser 200 includes a sleeve 202 and a syringe cartridge 204. The sleeve 202 is attached to the body 12 of the injector 10 and is designed to receive and retain the syringe cartridge 204. Any suitable attachment mechanism may be used to attach the sleeve 202 to the body 12 of the injector 10. For example, the sleeve 202 may be permanently attached to the body 12 of the injector 10 through a bonding process, a welding process, or by any other suitable means for permanent attachment. Alternatively, the sleeve 202 may be removably attached to body 12 of the injector 10 using, for example, a threading mechanism, a snap-fit connection, a male/female connection mechanism, or any other suitable mechanism providing non-permanent attachment. The sleeve 202 facilitates removable attachment of the syringe cartridge 204 and serves to protect the pneumatic cylinder 158 when the syringe cartridge 204 is removed.

FIG. 14 provides an exploded view of the sleeve 202, syringe cartridge 204, and the components which facilitate releasable mounting of the syringe cartridge 204 within the sleeve 202. As can be seen in FIG. 14, the sleeve 202 includes a spacer ring 206 and a locking ring 208. Once the sleeve is mounted to the body 12 of the injector 10, the locking ring 208 and the spacer ring 206 are maintained within the sleeve 202 by a retaining member 212, such as a ridge or any other suitable structure or device. The syringe cartridge 204 is advanced through the sleeve 202 until a seal 216 included at the proximal end 218 of the syringe cartridge 204 abuts the body 12 of the injector 10. Once the syringe cartridge 204 is fully advanced, it may be locked into place by applying a first torque, which causes locking members 223, included on the casing 219 of the syringe cartridge 204, to engage biased locking tabs 222 included in the locking ring 208. After use, the syringe cartridge 204 may be removed from the injector 10 by applying a second torque, which disengages the biased locking tabs 222 from the locking members 223 of the syringe cartridge 204. It is to be understood, however, that the dispenser 200 of the first embodiment of the injector 10 need not include a sleeve 202 and the syringe cartridge 204 may be permanently attached to the injector 10, particularly where the injector 10 is designed for a single use.

FIG. 15 provides a cross-sectional view of the syringe cartridge 204. As can be seen by reference to FIG. 15, the casing 219 of the syringe cartridge 204 houses a biasing mechanism 280 and a syringe 211 having a piston 270 and a needle 250, such as a hypodermic needle, through which medicament 220 is delivered. The biasing mechanism 280 supports the syringe 211 within the casing 219 and biases the reservoir 210 and needle 250 in a retracted position. The biasing mechanism 280 preferably includes a coil spring 282 through which the syringe 211 and needle 250 can be disposed.

The syringe cartridge 204 shown in FIG. 14 through FIG. 15 also includes an adjustable tip 230, which engages the distal end 221 of the casing 219 in any manner that permits the adjustable tip 230 to be advanced or retracted relative to the distal end 221 of the casing 219. For instance, the adjustable tip 230 may include a first threaded area and the distal end 221 of the casing 219 may include a second threaded area complimentary to the first threaded area, allowing the adjustable tip 230 to be advanced or retracted along the distal end 221 of the casing 219. However, the adjustable tip 230 may be mounted by any other suitable mechanism, such as a snap-fit mechanism or a ratchet fit mechanism, that allows the adjustable tip 230 to be advanced or retracted along the distal end 221 of the casing 219. Though the syringe cartridge 204 need not include an adjustable tip 230, providing the syringe cartridge with an adjustable tip 230 facilitates simple adjustment of the depth to which the needle 250 is inserted.

FIG. 16 through FIG. 22 illustrate a collapsible syringe cartridge 240 that may be used in an injector 10 according to the present invention. The collapsible syringe cartridge 240 includes a casing 219 having a collapsible portion 290 and a fixed portion 292. A syringe 211 serves as the reservoir 210. The syringe 211 terminates in a needle 250 of desired gauge and includes a piston 270. The collapsible syringe cartridge 240 further includes a bias mechanism 280 including a coil spring 282, which maintains the syringe 211 and needle 250 in a normally retracted position within the casing 219. Advantageously, the collapsible portion 290 of the casing 219 allows the use of a shorter piston 156, 170 within the driver 150 and thereby facilitates the construction of a shorter injector 10.

As can be seen in FIG. 5, FIG. 6, and FIG. 16 through FIG. 22, the casing 219 of the collapsible syringe cartridge 240 is designed to facilitate mounting of the collapsible syringe cartridge 240 within the body 12 of the injector 10. The casing 219 of the collapsible syringe cartridge 240 is not only shaped and sized to fit within a complimentary mounting area 242 provided in the body 12 of the injector 10, but the casing 219 also provides a suitable mechanism by which the collapsible syringe cartridge 240 may be mounted to an injector 10 of the present invention. For example, as is shown in FIG. 5, FIG. 6, and FIG. 16 through FIG. 22, the casing 219 may include a first threaded area that is complimentary to a second threaded area formed within the body 12 of the injector 10. Alternatively, the casing 219 of the collapsible syringe cartridge 240 may include one or more locking tabs 246 (shown in FIG. 20 through FIG. 22) complimentary to one or more recesses (not shown) formed within the body 12 of the injector 10. Though FIG. 5, FIG. 6, and FIG. 16 through FIG. 22 show collapsible syringe cartridges 240 including two specific mounting mechanisms, a collapsible syringe cartridge 240 useful with an injector 10 of the present invention may incorporate any other suitable mounting mechanism.

The collapsible portion 290 of the casing 219 is sized such that it can be displaced into and out of the fixed portion 292 of the casing 219. To help ensure that the collapsible portion 290 is not entirely displaced from the fixed portion 292, the distal end 293 of the collapsible portion 290 may be provided with a first lip 294 and the proximal end 295 of the fixed portion 292 may be provided with a second lip 296. As the collapsible portion 290 extends out of the fixed portion 292, the first lip 294 engages the second lip 296, which inhibits further extension of the collapsible portion 290 from the fixed portion 292. The collapsible portion 290 is also shaped and sized to receive the coil spring 282 that serves as the biasing mechanism 280. The coil spring 282 maintains the collapsible portion 290 in a normally extended position, which corresponds to the retracted position of the syringe 211 and needle 250.

The proximal end 297 of the collapsible portion 290 includes an orifice 298 sized to permit positioning of the syringe 212 within the collapsible the syringe cartridge 240. However, the orifice 298 is also sized to catch the proximal end 213 of the syringe 211 as the syringe 211 is positioned through the orifice 298. Thus, as an injection or insertion force is applied to the piston 270 included in the syringe 211 and the syringe 211 is displaced against the coil spring 282, the collapsible portion 290 is displaced with the syringe 211 into the fixed portion 292 of the casing 219 (shown in FIG. 19). Significantly, because the collapsible portion 290 is displaced within the fixed portion 292 of casing 219, the plunger 166 of the multistage or single stage piston 156, 170 included in the driver 150 need only be long enough to expel a desired dose of medicament 220 from the syringe 211. In contrast, where a syringe cartridge does not include a collapsible portion 290, such as the syringe cartridge 204 shown in FIG. 14 and FIG. 15, the plunger 166 of the piston 156, 170 must be long enough to both displace the syringe 211 within the syringe cartridge 204 and expel a desired dose of medicament 220.

Figure 20:
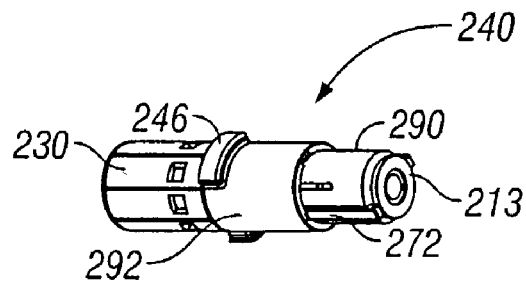
Figure 21:
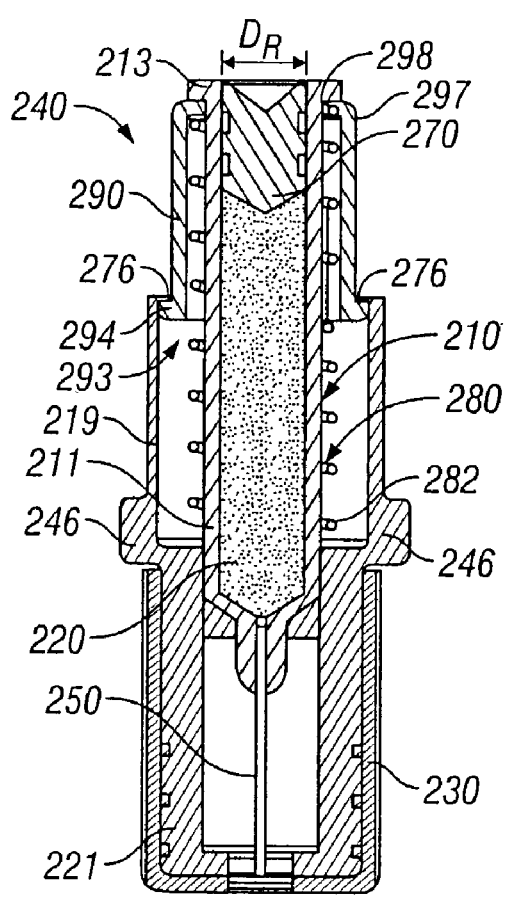
Figure 22:
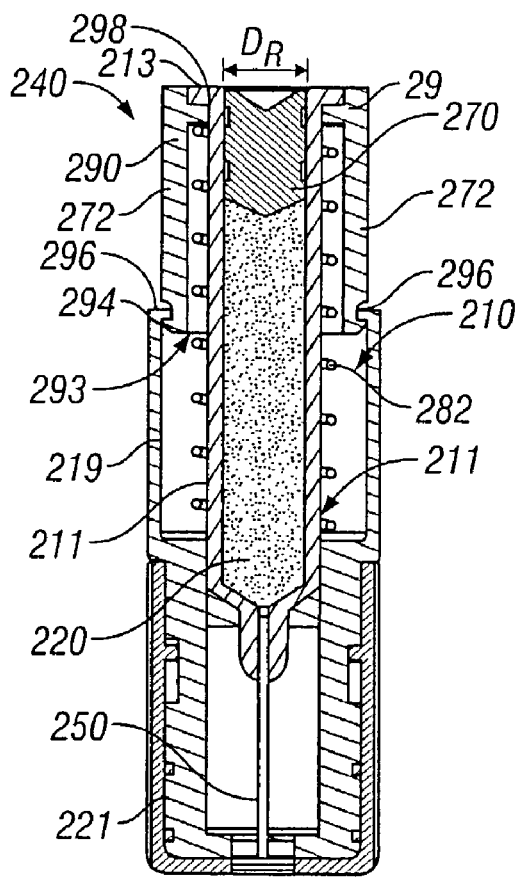

If desired, the collapsible syringe cartridge 240 may be provided with a locking mechanism that serves to minimize accidental compression of the syringe 211 before the collapsible syringe cartridge 240 is mounted to an injector 10. For example, as shown in FIG. 20 through FIG. 22, the collapsible portion may include one or more ears 272, which extend away from the outer surface of the collapsible portion 290. When the collapsible portion 290 is in a locked position, the one or more ears 272 cannot pass through the proximal end 295 of the fixed portion 292 of the casing 219, thereby preventing the collapsible portion 290 from being displaced within the fixed portion 292. In an unlocked position, the one or more ears 272 are aligned with one or more corresponding passages 276 provided in the proximal end 295 of the fixed portion 292 of the casing 219. The one or more corresponding passages 276 allow the one or more ears 272 to pass through the proximal end 295 of the fixed portion 292 of the casing 219, thereby allowing the collapsible portion 290 to be displaced within the fixed portion 292. Preferably, the body 12 of the injector 10 and the collapsible syringe cartridge 240 are designed such that mounting the collapsible syringe cartridge 240 to the injector 10 aligns the one or more ears 272 with the one or more corresponding passages 276, while removing the collapsible syringe cartridge 240 from the injector 10 misaligns the one or more ears 272 with one or more corresponding passages 276.

If desired, the collapsible syringe cartridge 240 may also include an adjustable tip 230, which engages the distal end 221 of the casing 219 in any manner that permits the adjustable tip 230 to be advanced or retracted relative to the distal end 221 of the casing 219. Again, the adjustable tip 230 may include a first threaded area complimentary to a second threaded area provided at the distal end 221 of the casing 219. However, adjustable tip 230 may be mounted by any other suitable mechanism, such as a snap-fit mechanism or a ratchet fit mechanism, that allows the adjustable tip 230 to be advanced or retracted along the distal end 221 of the casing 219.

The injector 10 of the present invention may also include a pressure relief mechanism for dissipating gas pressure developed within the pneumatic cylinder 158. For example, the injector 10 of the present invention may be designed to allow venting of pressurized gas once the piston 170 reaches a predetermined position within the pneumatic cylinder 158. As is shown in FIG. 5, the pneumatic cylinder 158 of the driver 150 may terminate in a vent chamber 500. The vent chamber 500 is sized so that the seal created between the piston 170 and the pneumatic cylinder 158 is broken as the piston 170 reaches the end of a predetermined stroke. Once the seal between the piston 170 and the pneumatic cylinder 158 is broken, pressurized gas escapes from the pneumatic cylinder 158 and into the vent chamber 500. The injector shown in FIG. 5 is designed such that pressurized gas moving into the vent chamber 500 is free to escape the injector 10 by flowing around or through the casing 219 of the dispenser 200. If desired, however, the vent chamber 500 may additionally include a fluid path (not shown) extending from the vent chamber 500, through the body 12 of the injector 10, and to the exterior surface 13 of the body 12. Such a fluid path may be desirable or necessary where more rapid venting of the pressurized gas is desired or where the design of the injector 10 does not permit pressurized gas flowing into the vent chamber 500 to escape around or through the dispenser 200.

FIG. 6 illustrates yet another pressure relief mechanism that may be incorporated into a plunger assembly 124 serving as the actuator 100 of an injector 10 of the present invention. Such a pressure relief mechanism includes a fluid path 510 formed within the body 130 of the plunger 128 of the plunger assembly 124. The fluid path 510 includes a vent 512 formed in the side of the plunger 128. When the vent 512 is located on the interior side of sealing member 18 of the plunger assembly 124, a sealed environment is maintained within the injector 10. However, if the plunger 128 is displaced such that the vent 512 is located on the exterior side of the sealing member, fluid communication between the interior and exterior of the injector 10 is permitted. As the plunger 128 is depressed and the microcylinder 52 is compromised, the pressurized gas escaping from the microcylinder 52 enters the fluid path 510 and acts against the plunger 128, creating a displacement force sufficient to displace the plunger 128 such that the vent 512 is positioned on the exterior side of the sealing member 18. However, as long as the plunger 128 is depressed with a force equal to or greater than the displacement force resulting from the pressurized gas, the plunger 128 will not be displaced and fluid communication between the interior of the injector 10 and the exterior environment will be prevented. Once the plunger 128 is released, however, such as at the end of the delivery cycle, the plunger 128 will be displaced such that the vent 512 is positioned on the exterior side of the sealing element 18 and pressurized gas contained within the injector 10 will exit the injector 10 through the plunger 128.

Where, the injector 10 includes a safety mechanism 20, the safety mechanism 20 may be designed to help ensure proper functioning of the pressure relief mechanism shown in FIG. 6. For instance, as shown in FIG. 6, the width of the slot 30 included in the first portion 22 of the safety mechanism 20 is smaller than the width of the body 130 of the plunger 128. Thus, when the safety mechanism 20 is moved out of the safe position, the plunger 128 can not be displaced to such an extent that the vent 512 formed in the plunger 128 is positioned on the exterior side of the sealing member 18. However, as the safety mechanism 20 moves back into the safe position, the slot 30 opens into port 31, which is sized to allow the body 130 of the plunger 128 to be displaced such that the orifice 512 is positioned on the exterior side of the sealing member 18. Moreover, the stop 32 of the safety mechanism 20 may include a lip 33, which prevents the plunger 128 from being entirely expelled from the passageway 126 of the plunger mechanism 124. Thus, the injector 10 of the present invention may include a safety mechanism 20 which not only minimizes the possibility of accidentally firing the injector 10, but which also works in concert with a venting mechanism to ensure that pressurized gas is properly vented from the injector 10.

Significantly, the driver 150 and dispenser 200 of the injector 10 of the present invention need not be separate devices. As shown in FIG. 23 and FIG. 24, the dispenser 200 may incorporate the driver to simplify construction of injector 10. In such an instance, the reservoir 210, such as a syringe 211, of the dispenser 200 serves as at least a portion of the pneumatic cylinder of the driver, and the piston 270 of the dispenser 200 may be designed as a single stage piston 156 or a multistage piston 170 that acts directly against medicament 220 contained within the reservoir 210. As it reduces the size of the injector 10 and decreases the amount of materials used to manufacture the injector 10, incorporating the driver within the dispenser 200 provides a more economical and portable device. Where the driver and dispenser 200 are integrated, however, the cross-sectional diameter of the piston 156, 170 is limited to the maximum interior diameter of the reservoir 210. Though the injectors 10 illustrated in FIG. 23 and FIG. 24 do not include a pressure regulator or a restrictor, if desired, injectors 10 including an integrated driver and dispenser 200 may be provided with a pressure regulator or restrictor, such as those already described.

In addition, the injector of the present invention may be designed for a single use or for multiple uses. Where the injector is designed for a single use, each of the components of the injector are designed to be disposed after a single use and may be permanently integrated into a single housing. However, where the injector of the present invention is designed as a multiple use injector, at least one of the components of the injector is designed for repetitive use. Regardless of whether or not the actuator and driver a multiple use injector of the present invention are designed as discrete devices, both the pressurized gas source and the dispenser of a multi-use injector according to the present invention will are preferably be designed as modular components. Such a design facilitates the easy attachment and detachment of the pressurized gas source and the dispenser to and from the actuator or the driver of the injector.

The injector of the present invention is desirable because the design of the injector is flexible, allowing the injector of the present invention to be designed to deliver medicaments exhibiting a wide range of viscosities. In particular, the injector of the present invention is well suited for the delivery of viscous medicaments and may be designed to deliver viscous medicaments having viscosities of 1 Poise or greater, 10 Poise or greater, 20 Poise or greater, 50 Poise or greater, or even 100 Poise or greater. Generally, the injector of the present invention will be configured to exert an injection force ranging from about 5 lbs. to about 200 lbs. However, the design of the injector of the present invention is not limited to an injector providing an injection force falling within the range of between about 5 lbs. and 200 lbs. The injector of the present invention may be configured to exert any desired injection force tailored to ensure delivery of a desired dose of a chosen medicament within a desired amount of time.

The Hagen-Poiseuille Law may be used to determine the injection force required to deliver a desired dose of a chosen medicament within a predetermined amount of time. For example, in order to deliver 0.5 cc of a medicament having a viscosity of 200 Poise within 10 seconds via a syringe having an internal diameter of 4.5 mm and a 0.5 inch needle having an internal diameter of 0.012 inches (a 24 gauge needle), the Hagen-Poiseuille Law indicates that an injection force of approximately 100 pounds is required. Such a force determination maybe undertaken for any dose of any chosen medicament that is to be delivered through a chosen syringe and needle. As is easily appreciated, even when the viscosity of the medicament remains constant, adjusting one or more of the variables represented in the Hagen-Poiseuille Law will result in a different required injection force. Therefore, even where the Theological properties of the medicament to be delivered remain the same, greater or lesser injection forces may be needed, depending on, for example, the desire delivery time, the length and gauge of the needle to be used, and the diameter of the syringe or other reservoir used to contain the medicament before it is expelled through the needle.

Once the desired injection force is determined, the various components of the injector of the present invention may be adapted to generate a desired force, forces, or force profile. As can be appreciated from the foregoing description, the pressurized gas source and driver of the injector of the present invention can be configured to achieve a desired force, forces, or force profile. For example, a pressure of 197 psi can be achieved within a pneumatic cylinder having an internal diameter of 0.75 inches and an internal length of 2.50 inches by providing the injector of the present invention with a commercially available microcylinder having internal measuring 0.35 inches×1.50 inches and containing gas stored at 1,750 psi. As the internal diameter of the pneumatic cylinder equals 0.75 inches, the injection stage of a single stage or multistage piston included within the driver would also measure 0.75 inches, resulting in the generation of an injection force of 87 lbs. Additionally, if a pressure of 197 psi is produced within the pneumatic cylinder, providing a the driver with a multistage piston having an insertion stage measuring 0.20 inches in diameter would result in the generation of an insertion force of 6 lbs. If substantially constant insertion or injection forces are required or desired, the injector of the present invention may be configured to include a pressure regulator or restrictor, such as those already described herein. Although the injector of the present invention is preferably configured to generate injection forces ranging between about 5 lbs. and about 120 lbs., and, where desired, to provide insertion forces or effective insertion ranging between about 1 lbs. and 7 lbs., the injector of the present invention is not limited to such configurations and may be designed to provide desired injection or insertion forces falling outside those presently preferred ranges.

In addition, the injector of the present invention is desirable because the drive mechanism of the injector is relatively simple and operates relatively quietly, without the transmission of significant impact or recoil forces. Where the injector of the present invention includes a multistage driver, the injector of the present invention is capable of generating insertion and injection forces using a single driving mechanism. Moreover, the specifications and configuration of the pressurized gas source and driver of the injector of the present are easily adjusted to provide insertion forces that minimize subject discomfort, while providing injection forces that maximize delivery efficiency of even highly viscous medicaments. Even where the injector of the present invention includes a single stage driver, the injector of the present invention may be designed to generate an injection force suitable for delivering a desired dose of a chosen medicament, while providing an effective insertion force tailored to minimize subject discomfort. Due to the simplicity of the pneumatic driving mechanism used in the injector of the present invention, moving parts within the injector are limited and operate relatively unobtrusively, allowing the injector of the present invention to function without generating excess noise or transmitting significant impact or recoil forces.

The components of the injector of the present invention may be manufactured using any suitable materials and known manufacturing processes. For example, known metals, metal alloys, composites, or natural or synthetic rubber or polymer materials may be used to fabricate the dispenser, the driver, the actuator, and, where included in the pressurized gas source, the cap. Moreover, suitable glass materials may be used in the fabrication of one or more components of the dispenser. Such materials may be molded, machined, cast, or formed through other suitable manufacturing process to produce components of desired shape and size. Specific materials that may be used to fabricate one or more of the various components and subcomponents of the injector of the present invention include, for example, aluminum and aluminum alloys, stainless steel, such as 304 or 316 stainless steel, glass reinforced nylon, liquid crystal polymer (LCP), PEEK polymer, and Delryn polymer. Of particular use in fabricating the reservoir and casing of the dispenser of the injector of the present invention are 304 stainless steel, 316 stainless steel, LCP, and PEEK polymer. However, as will be appreciated by those of skill in the art, the injector of the present invention may be fabricated using any material and manufacturing process providing an injector capable of withstanding the anticipated operational stresses of an injector designed according to the present invention.

The present invention also includes a method of injecting viscous medicaments. In each of its embodiments, the method of the present invention includes providing a medicament, providing a needle of a desired gauge, inserting the needle into the tissue of the subject, and generating an injection force sufficient to drive the viscous medicament through the needle and into the tissue of the subject. Preferably, the medicament provided in the method of the present invention is a viscous medicament (i.e., a medicament having a viscosity greater than 1 Poise). Even more preferably, the method of the present invention includes providing a medicament having a viscosity of 10 Poise or greater, 20 Poise or greater, 50 Poise or greater, or 100 Poise or greater. Though the medicament provided in the method of the present invention is preferably a viscous medicament, the method of the present invention is not so limited and may include providing a medicament exhibiting a viscosity below 1 Poise.

Because the comfort of the subject generally increases as the gauge of the needle decreases (i.e., the inner diameter of the needle decreases), the needle provided in the method of the present invention preferably has a gauge ranging between 21 gauge and 31 gauge. Even more preferably, the gauge of the needle provided in the method of present invention ranges between 24 gauge and 31 gauge, and most preferably, the gauge of the needle provided in the method of the present invention ranges between 27 and 31 gauge. However, such needle gauge ranges are simply presently preferred ranges. The gauge of the needle used in the method of the present invention will vary depending on, for example, the viscosity of the medicament to be injected, the nature of the subject, the tissue of the subject where the injection will take place, the injection force generated, and the desired time for injection. Therefore, the gauge and length of the needle used in the method of the present invention may vary with the desired application.

Further, the injection force generated in the method of the present invention is sufficient to deliver a desired dose of the provided medicament within a suitable amount of time. Preferably, the injection force is sufficient to deliver a desired dose of the provided medicament within 10 seconds. Even more preferably, the injection force generated in the method of the present invention is sufficient to deliver a desired dose of the provided medicament within 5 seconds. In order to accomplish delivery of a desired dose of the provided medicament within the presently preferred times, the injection force generated in the method of the present invention will generally range between about 5 lbs. and 200 lbs. However, as is true of each of the other aspects of the method of the present invention, the magnitude of the injection force generated in the method of the present invention is variable and will depend on, for example, the dispenser provided, the medicament provided and the dose of the medicament to be delivered. The injection force generated in the method of the present invention need only be of sufficient magnitude to deliver a desired dose of the provided medicament within a suitable amount of time. Thus, depending upon the application, the injection force generated in the method of the present invention may be lower than 5 lbs. or higher than 200 lbs. Moreover, the method of the present invention is not limited to the generation of injection forces sufficient to deliver a desired dose of the provided medicament within the presently preferred amounts of time.

In another embodiment, the method of the present invention further includes providing an insertion force or an effective insertion force, which is less than the injection force and may be tailored to minimize subject discomfort as the needle is inserted into the tissue of the subject. For example, where the intended subject is human and the gauge of the needle provided ranges from between 21 gauge and 31 gauge, an insertion force of between about 1 pound and 7 pounds is presently preferred, with an injection force of between about 1 and 4 pounds being even more preferable. However, the magnitude of an insertion generated in the method of the present invention may vary according to several factors, such as the anticipated subject, the gauge of the needle to be inserted into the tissue of the subject, and the desired avenue of injection (e.g., subcutaneous, intramuscular, or intra-articular. Further, where the method of the present invention includes providing an insertion force, both the injection force and the insertion force are preferably generated using a single drive mechanism.

Figures 26, 27, 28, 29:
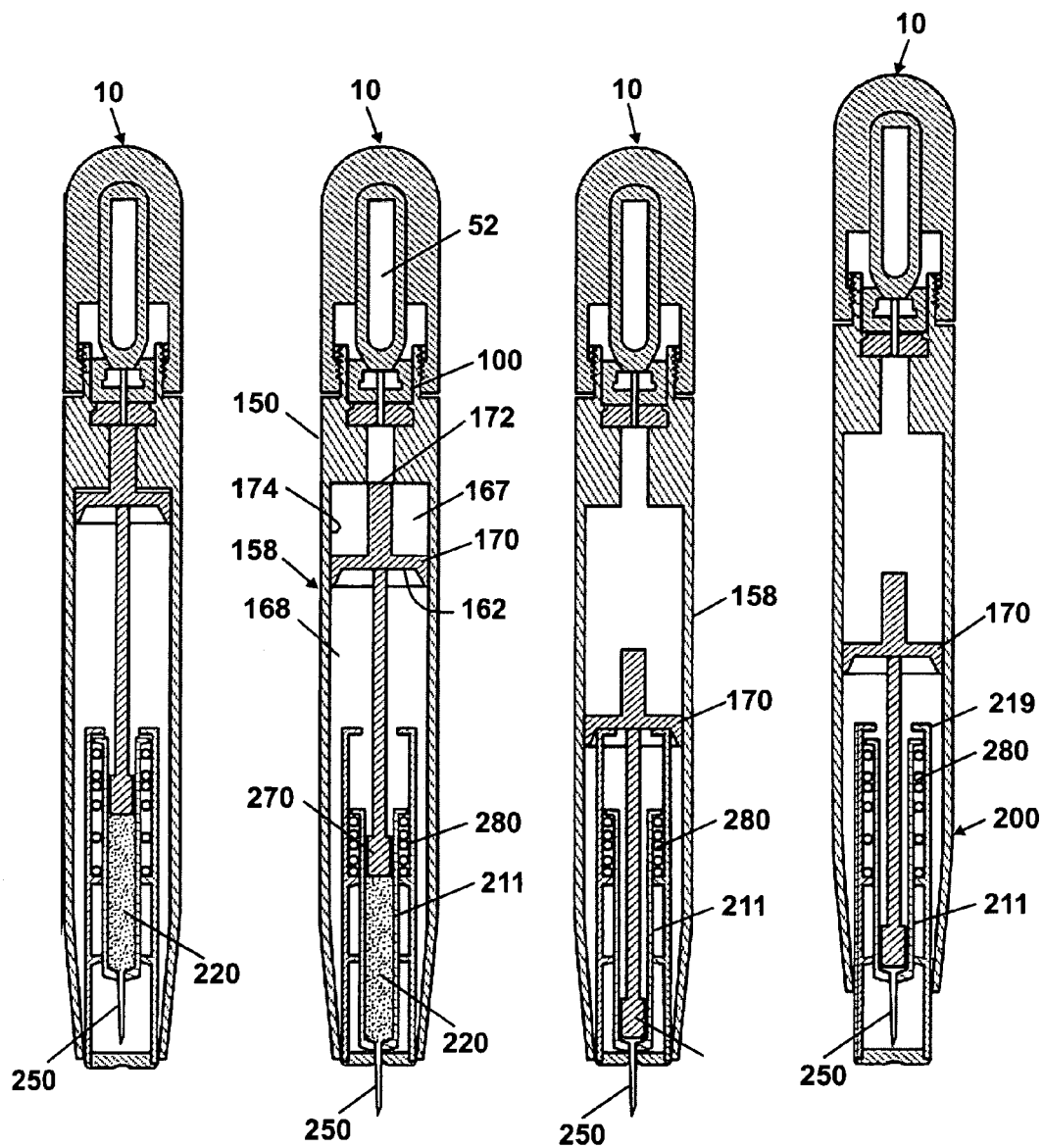
FIG. 26 through FIG. 29 illustrate one embodiment of the method of the present invention.

In each of its embodiments, the method of the present invention may further include providing an injector of the present invention. For example, FIG. 26 through FIG. 29 illustrate one embodiment of the method of the present invention carried out with an injector 10 according to the present invention. FIG. 26 illustrates the injector 10 providing a needle 250 and a medicament 220. The injector may be placed against the tissue (not shown) of a subject. As shown in FIG. 27, actuation of the actuator 100 causes pressurized gas from the microcylinder 52 to the driver 150, and as pressurized gas acts against the insertion stage 172 of the multistage piston 170, an insertion force is generated, which drives the syringe 211 and needle 250 against the bias mechanism 280 and into the tissue (not shown) of the subject. Once the seal formed between the insertion stage 172 and the wall 174 of the first chamber 167 of the pneumatic cylinder 158 breaks, pressurized gas acts against the injection stage 162 of the multistage piston 170, providing an injection force. The injection force is greater than the insertion force and is transmitted to the plunger 270 of the syringe 211. As the multistage piston 170 is driven through the second chamber 168 of the pneumatic cylinder 158 with the injection force, the plunger 270 drives a desired dose of medicament 220 from the syringe 211 and into the tissue (not shown) of the subject (shown in FIG. 28). Preferably, once a desired amount of medicament 220 is delivered, the forward progress of the multistage piston 170 terminates and the pressure within the pneumatic cylinder 158 dissipates. As the pressure within the pneumatic cylinder 158 dissipates, the force transmitted by the multistage piston 170 to plunger 270 also dissipates and becomes incapable of overcoming the bias force exerted by the biasing mechanism 280. As the force exerted by the multistage piston 170 is no longer equal to or greater than the bias force exerted by the bias mechanism 280, the syringe 211 and needle 250 are automatically retracted by the bias mechanism 280 into the casing 219 of the dispenser 200 (shown in FIG. 29).

The embodiment of the method of the present invention illustrated in FIG. 26 through FIG. 29, however, is merely exemplary and does not limit the scope of the method of the present invention. In particular, the method of the present invention is not limited to providing the injector illustrated in FIG. 26 through FIG. 29. Any injector of the present invention may be used to carry out one or more embodiments of the method of the present invention.

EXAMPLE 1

Figure 25:
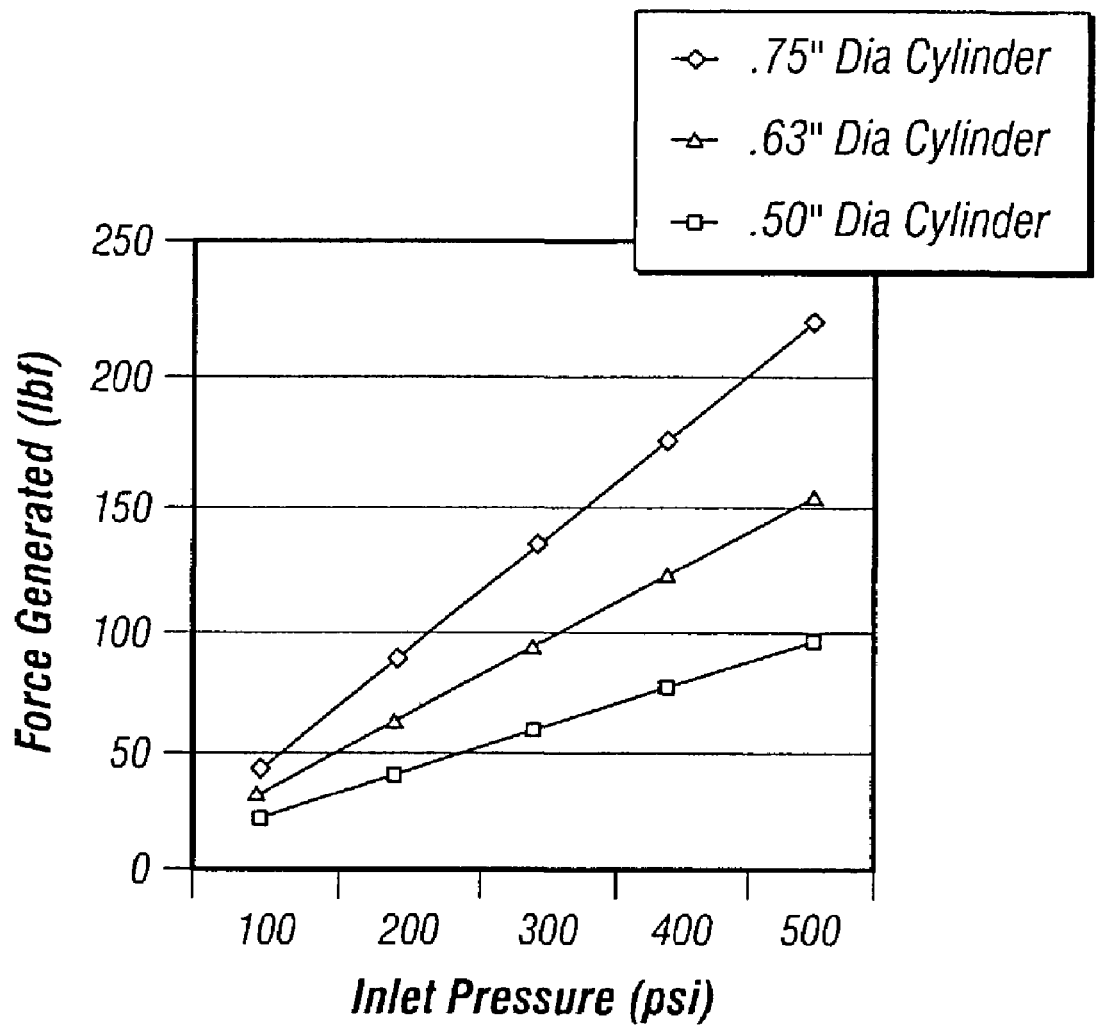
FIG. 25 provides a graph illustrating that the forces exerted by the injector of the present invention may be increased or decreased by increasing or decreasing the pressure generated within the pneumatic cylinder of the driver or by increasing or decreasing the surface area of the piston included within the driver.

FIG. 25 provides a graph illustrating that the forces exerted by the injector of the present invention may be adjusted simply by altering the pressure generated within the pneumatic cylinder of the driver of the injector or by altering the surface area of the piston included within the driver. As can be appreciated by reference to the graph, where a given pressure is generated, the forces exerted by the piston increase as the diameter of the piston increases and decrease as the diameter of the piston decreases. In addition, where a piston of a given diameter is provided, the forces exerted by the piston increase as the pressure within the pneumatic cylinder increases and decrease as the pressure within the pneumatic cylinder decreases. Therefore, the information graphed in FIG. 25 illustrates that the force, forces, or force profiles exerted by the driver of an injector of the present invention may tailored to suit one or more desired applications simply by altering the pressure generated within the pneumatic cylinder of the driver or by altering the surface area of the insertion or injection stages included in the multistage or single stage piston provided within the pneumatic piston.

EXAMPLE 2

An injector according to the present invention was tested to determine the injection time required to deliver a material of chosen viscosity through needles having different gauges. The injector used in the tests utilized a pressurized gas source including a commercially available 12 gram sealed microcylinder that was filled with 0.2 grams of nitrogen at 1,750 psi. The actuator of the injector included a piercing mechanism, and threading a cap containing the sealed microcylinder onto the body of the injector such that the seal of the microcylinder was compromised by the piercing mechanism actuated the injector. The injector included a restrictor formed of a plate having an orifice measuring 0.0015 inches in diameter, and the restrictor was positioned between the piercing mechanism of the actuator and the driver of the injector. The driver of the injector was a multistage driver including a pneumatic cylinder having first and second chambers and a multistage piston including an insertion stage and an injection stage. The pneumatic cylinder was 2.50 inches in length and had a maximum internal diameter of 0.75 inches. The insertion stage of the multistage piston measured 0.2 inches in diameter, and the injection stage of the multistage piston measured 0.75 inches in diameter. Upon actuation of the injector, the multistage driver generated an insertion force of about 6 lbs. and an injection force of about 84 lbs.

In each test the injector was provided with a dispenser having a sleeve and syringe cartridge as illustrated in FIGS. 14 and 15. In each test the syringe of the syringe cartridge was pre-filled with 0.5 cc of a non-Newtonian formulation having a static viscosity of about 1,000 Poise and a dynamic viscosity of about 200 Poise as measured at a 1.0 sec-1 shear rate and 25° C. using a Haake Rheometer. However, the syringe cartridge provided in the first test included a 0.5 inch 24 gauge needle, while the syringe cartridge provided in the second test included a 0.5 inch 27 gauge needle. Before each test, the formulation was heated to between about 41° C. and 43° C.

The results of the tests show that the gauge of the needle directly affects the time required to deliver a chosen formulation, all else being the same. However, in each test the desired amount of the chosen formulation was delivered well within 10 seconds. Moreover, in each test the injector produced very little noise and did not transmit noticeable impact or recoil forces.

What is claimed is:

1. A device for injecting a viscous medicament comprising:
   a body comprising a dispenser having a reservoir for containing the viscous medicament and a needle suitable for injecting the medicament, wherein the gauge of the needle is equal to or greater than about 21 gauge;
   a cap adapted for attachment to the body, the cap comprising a pressurized gas source, wherein the pressurized gas source includes a microcylinder of compressed gas;
   a driver situated between the cap and dispenser and activated by flow of pressurized gas from the pressurized gas source and arranged to exert an insertion force and an injection force against the dispenser, the injection force being of sufficient magnitude to drive the viscous medicament through the needle with sufficient force to cause injection of the medicament;
   a bias mechanism which retains the reservoir and needle in a retracted position within the dispenser until the driver exerts the insertion force against the dispenser; and
   an actuator adjacent the pressurized gas source and configured to compromise the microcylinder to initiate the flow of pressurized gas from the pressurized gas source to the driver.

2. The device of claim 1, wherein the viscous medicament has a viscosity greater than about 10 poise.

3. The device of claim 1, wherein the viscous medicament has a viscosity greater than about 50 poise.

4. The device of claim 1, wherein the viscous medicament has a viscosity greater than about 100 poise.

5. The device of claim 1, wherein the driver comprises a multistage piston configured to exert the insertion force and the injection force against the dispenser, the second force being greater than the first force.

6. The device of claim 5, wherein the multistage piston is configured such that the insertion force is less than or equal to about 7 lbs and the insertion force is sufficient to inject the viscous medicament through the needle.

7. The device of claim 1, wherein the gauge of the needle ranges from about 27 gauge to about 31 gauge.

8. The device of claim 1, wherein the device is configured to inject up to about 0.5 cc of the viscous medicament through the needle within about 10 seconds.

9. The device of claim 1, wherein the device is configured to inject about 0.5 cc of the viscous medicament through the needle within about 5 seconds.

10. The device of claim 1, wherein the pressurized gas source, driver, and dispenser are configured to inject up to about 0.5 cc of the viscous medicament through the needle within about 10 seconds.

11. The device of claim 10, wherein the pressurized gas source, driver, and the dispenser are configured to inject up to about 0.5 cc of the viscous medicament through the needle within about 5 seconds.

12. The device of claim 1, wherein the actuator comprises a valve to actuate flow of pressurized gas from the pressurized gas source to the driver.

13. A device for injecting a viscous medicament, comprising:
   a dispenser having a reservoir for containing a viscous medicament and a needle suitable for injecting the medicament, wherein the gauge of the needle is equal to or greater than about 21 gauge;
   a pressurized gas source;
   a driver activated by flow of pressurized gas from the pressurized gas source, wherein the driver comprises a multistage piston having at least an insertion stage characterized by a first surface area and an injection stage characterized by a second surface area larger than the first surface area, said driver being configured such that the flow of pressurized gas acts sequentially against the insertion stage and the injection stage to exert at least an insertion force and an injection force sequentially against the dispenser;
   a bias mechanism having a spring force sufficient to bias the reservoir and needle in a retracted position within the dispenser until the driver exerts the insertion force against the dispenser; and
   an actuator which initiates the flow of pressurized gas from the pressurized gas source to the driver.

14. The device of claim 13, wherein the injection force is greater than the insertion force.

15. The device of claim 14, wherein the insertion force is less than or equal to about 7 lbs and the injection force is sufficient to inject the viscous medicament through the needle.

16. A method for injecting a viscous medicament, the method comprising:
   providing a viscous medicament in a device having a cap comprising a pressurized gas source including a microcylinder of compressed gas, a body comprising a dispenser having a reservoir for containing the viscous medicament and a needle for injecting the viscous medicament, the needle having a needle gauge that is equal to or greater than about 21 gauge, a driver situated between the cap and the dispenser, the driver comprising a multistage piston having at least an insertion stage and an injection stage, and an actuator adjacent the pressurized gas source;
   activating the actuator to compromise the microcylinder and initiate flow of pressurized gas from the pressurized gas source; and
   transmitting the flow of pressurized gas to the driver to exert an insertion force and an injection force sequentially on the dispenser, the injection force being of sufficient magnitude to drive the viscous medicament through the needle.

17. The method according to claim 16, wherein providing the viscous medicament comprises providing a medicament exhibiting a viscosity equal to or greater than about 10 poise.

18. The method according to claim 16, wherein providing the viscous medicament comprises providing a medicament exhibiting a viscosity equal to or greater than about 50 poise.

19. The method according to claim 16, wherein providing the viscous medicament comprises a medicament exhibiting a viscosity equal to or greater than about 100 poise.

20. The method according to claim 16, wherein the needle gauge is equal to or greater than about 27 gauge.

21. The method according to claim 16, wherein the needle gauge is equal to about 31 gauge.

* * * * *